(12) United States Patent
Sinha

(10) Patent No.: US 8,820,147 B2
(45) Date of Patent: Sep. 2, 2014

(54) MULTIPHASE FLUID CHARACTERIZATION SYSTEM

(75) Inventor: Dipen N. Sinha, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 487 days.

(21) Appl. No.: 13/226,209

(22) Filed: Sep. 6, 2011

(65) Prior Publication Data

US 2012/0055239 A1   Mar. 8, 2012

Related U.S. Application Data

(60) Provisional application No. 61/379,919, filed on Sep. 3, 2010.

(51) Int. Cl.
*G01N 29/00* (2006.01)

(52) U.S. Cl.
USPC ........................................................ 73/61.79

(58) Field of Classification Search
CPC .................. G01N 29/032; G01N 2291/02836
USPC .............................................. 73/19.03, 61.79
See application file for complete search history.

(56) References Cited

U.S. PATENT DOCUMENTS

| 5,767,407 A | 6/1998 | Sinha |
| 6,918,875 B2 | 7/2005 | Moriya et al. |
| 6,959,601 B2 | 11/2005 | Sinha |
| 7,437,946 B2 | 10/2008 | Gysling |
| 2007/0006640 A1 | 1/2007 | Gysling |

OTHER PUBLICATIONS

"Method for Noninvasive Determination of Acoustic Properties of Fluids Inside Pipes," by Dipen N. Sinha et al., filed on Sep. 6, 2011.
"Apparatus and Method for Noninvasive Particle Detection Using Doppler Spectroscopy," by Dipen N. Sinha filed on Sep. 6, 2011.
International Search Report for PCT/US11/50569, International Searching Authority, Jan. 5, 2012, pp. 1-13.

*Primary Examiner* — Peter Macchiarolo
*Assistant Examiner* — Alex Devito
(74) *Attorney, Agent, or Firm* — Samuel M. Freund; Cochran Freund & Young LLC

(57) ABSTRACT

A measurement system and method for permitting multiple independent measurements of several physical parameters of multiphase fluids flowing through pipes are described. Multiple acoustic transducers are placed in acoustic communication with or attached to the outside surface of a section of existing spool (metal pipe), typically less than 3 feet in length, for noninvasive measurements. Sound speed, sound attenuation, fluid density, fluid flow, container wall resonance characteristics, and Doppler measurements for gas volume fraction may be measured simultaneously by the system. Temperature measurements are made using a temperature sensor for oil-cut correction.

34 Claims, 16 Drawing Sheets

Multiple bubbles

Single bubble

US 8,820,147 B2

MULTIPHASE FLUID CHARACTERIZATION SYSTEM

CROSS-REFERENCE TO RELATED APPLICATIONS

The present application claims the benefit of U.S. Provisional Patent Application No. 61/379,919 for "Noninvasive Multiphase Fluid Characterization System" which was filed on Sep. 3, 2010, the entire contents of which is hereby specifically incorporated by reference herein for all that it discloses and teaches.

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates generally to a method for determining the composition of fluids flowing through pipes and, more particularly, to an apparatus and method for independently measuring several physical parameters of multiphase fluids (a mixture of discrete phases, such as a mixture including oil, gas, and water phases) flowing through pipes.

BACKGROUND OF THE INVENTION

In many industries, in particular in oil production, the determination of multiphase fluid (e.g., oil/water/gas) composition and flow are important for determining how much fluid of any given phase is generated in a reservoir and is being pumped out or transported through pipes. There are many commercial instruments currently used that can provide this information, but since no one device can make all the required measurements, separate instruments of different types from multiple manufacturers are typically required to provide a complete answer. For example, one instrument may measure fluid flow, whereas another one measures the fluid composition.

Often these instruments have severe constraints and limited range of operation. For example, capacitance probes for measuring oil/water composition do not work well when the fluid becomes water continuous. Coriolis flowmeters are mass flowmeters that can also be operated as vibrating tube densitometers. The density of each phase may be used to convert the mass flow rate for a particular phase into a volumetric measurement. Numerous difficulties exist in using a Coriolis flowmeter to identify the respective mass percentages of oil, gas, and water in a total combined flow stream, particularly when there is gas present in the liquid.

Additionally, most of the fluid property measuring instruments require the flow to be diverted out of a principal flow pipe and into that particular instrument. Others require physical contact between the sensor and the fluid, which require a lot of maintenance for caustic fluids. The present invention allows measurements of multiple parameters of a multiphase system using noninvasive techniques where the sensors are attached on the outside of an existing pipe or on a small spool that is inserted in the line and all the sensors are acoustics based except the temperature sensor.

SUMMARY OF THE INVENTION

Embodiments of the present invention overcome the disadvantages and limitations of the prior art by providing a system and method for independently measuring chosen parameters of a multiphase fluid.

Another object of embodiments of the present invention is to provide a system and method for independently measuring chosen parameters of a multiphase fluid where the measurements are made without having to divert the fluid out of its principal flow path.

Yet another object of embodiments of the present invention is to provide a system and method for noninvasively and independently measuring chosen parameters of a multiphase fluid.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein the system for noninvasively measuring multiple independent physical parameters of a multiphase fluid comprising at least one liquid component and gas bubbles flowing in a pipe having a wall, an outside surface and an axis, hereof, includes: a first transmitting transducer in ultrasonic communication with the outside surface of the pipe; a first waveform generator for generating a frequency chirp signal for driving the first transmitting transducer; a first receiving transducer in ultrasonic communication with the outside surface of the pipe diametrically opposed to the first transmitting transducer for receiving the frequency chirp signal from the first transmitting transducer after the chirp signal passes through the multiphase fluid, and for generating a first electrical signal in response thereto; means for receiving the first electrical signal from the first receiving transducer and the frequency chirp signal generated by the waveform generator, and for generating speed of sound and sound attenuation information therefrom, from which the composition of the at least one component of the multiphase fluid is determined; a second transmitting transducer in ultrasonic communication with the outside surface of the pipe; a third transmitting transducer in ultrasonic communication with the outside surface of the pipe disposed a known distance along the axis of the pipe from the second transmitting transducer; a second waveform generator for generating a first fixed frequency signal for driving the second transmitting transducer and the third transmitting transducer; a second receiving transducer in ultrasonic communication with the outside surface of the pipe diametrically opposed to the second transmitting transducer for receiving the first fixed frequency signal from the second transmitting transducer after the fixed frequency signal passes through the multiphase fluid, and for generating a second electrical signal in response thereto; a third receiving transducer in ultrasonic communication with the outside surface of the pipe diametrically opposed to the third transmitting transducer for receiving the first fixed frequency signal from the third transmitting transducer after the fixed frequency signal passes through the multiphase fluid, and for generating a third electrical signal in response thereto; means for receiving the second electrical signal and the third electrical signal, whereby a disturbance in the fluid affecting the second electrical signal will affect the third electrical signal at a later time from which the flow rate of the fluid is calculated; a fourth transmitting transducer in ultrasonic communication with the outside surface of the pipe; a third waveform generator for generating a second fixed frequency signal for driving the fourth transmitting transducer; a fourth receiving transducer in ultrasonic communication with the outside surface of the pipe disposed in the vicinity of the fourth transmitting transducer at the same position along the axis of the pipe as the fourth transmitting transducer for receiving a Doppler shifted second fixed frequency signal resulting from reflection from gas bubbles in the multiphase fluid, and for generating a fourth electrical signal in response thereto; and means for receiving the fourth electrical signal and the second fixed frequency signal from the third waveform generator, and for determining the signal strength of the Doppler shifted second fixed frequency signal from which the volume of gas bubbles is determined.

In another aspect of the present invention and in accordance with its objects and purposes, the method for noninvasively measuring multiple independent physical parameters of a multiphase fluid comprising at least one liquid component and gas bubbles flowing in a pipe having a wall, an outside surface and an axis, hereof, includes: generating a frequency chirp signal for driving a first transmitting transducer in ultrasonic communication with the outside surface of said pipe; receiving the generated frequency chirp signal on a first receiving transducer in ultrasonic communication with the outside surface of said pipe diametrically opposed to the first transmitting transducer after the chirp signal passes through said multiphase fluid, and generating a first electrical signal in response thereto; receiving the first electrical signal and the generated frequency chirp signal, and generating speed of sound and sound attenuation information therefrom, from which the composition of the at least one component of said multiphase fluid is determined; generating a first fixed frequency signal for driving a second transmitting transducer in ultrasonic communication with the outside surface of said pipe, and a third transmitting transducer in ultrasonic communication with the outside surface of said pipe disposed a known distance along the axis of said pipe from the second transmitting transducer; receiving the first fixed frequency signal on a second receiving transducer in ultrasonic communication with the outside surface of said pipe diametrically opposed to the second transmitting transducer after the first fixed frequency signal passes through said multiphase fluid, and generating a second electrical signal in response thereto; receiving the first fixed frequency on a third receiving transducer in ultrasonic communication with the outside surface of said pipe diametrically opposed to the third transmitting transducer after the first fixed frequency signal passes through said multiphase fluid, and generating a third electrical signal in response thereto; receiving the second electrical signal the third electrical signal and calculating the flow rate of said multiphase fluid from a disturbance in the fluid affecting the second electrical signal and affecting the third electrical signal at a later time; generating a second fixed frequency signal for driving a fourth transmitting transducer in ultrasonic communication with the outside surface of said pipe; receiving a Doppler shifted second fixed frequency signal resulting from reflection from said gas bubbles on a fourth receiving transducer in ultrasonic communication with the outside surface of said pipe disposed in the vicinity of the fourth transmitting transducer at the same position along the axis of said pipe as the fourth transmitting transducer and for generating a fourth electrical signal in response thereto; and receiving the fourth electrical signal and the second fixed frequency signal and determining the signal strength of the Doppler shifted second fixed frequency signal from which the volume of said gas bubbles is determined.

In still another aspect of the present invention and in accordance with its objects and purposed, the method for noninvasively measuring multiple independent physical parameters of a multiphase fluid comprising at least one liquid component and gas bubbles flowing in a pipe having a wall, an outside surface and an axis, hereof, includes: generating an ultrasonic frequency chirp signal in the multiphase fluid; receiving the generated frequency chirp signal after the chirp signal passes through the multiphase fluid, and generating a first electrical signal in response thereto; receiving the first electrical signal and the generated frequency chirp signal, and generating speed of sound and sound attenuation information therefrom, from which the composition of the at least one component of the multiphase fluid is determined; generating a first fixed ultrasonic frequency signal and a second fixed ultrasonic frequency signal disposed a known distance along the axis of said pipe from the first fixed frequency signal in the multiphase liquid; receiving the first fixed frequency signal after the first fixed frequency signal passes through the multiphase fluid, and generating a second electrical signal in response thereto; receiving the second fixed frequency signal after the second fixed frequency signal passes through said multiphase fluid, and generating a third electrical signal in response thereto; receiving the second electrical signal and the third electrical signal and calculating the flow rate of the multiphase fluid from a disturbance in the fluid affecting the second fixed frequency electrical signal and affecting the third electrical signal at a later time; generating a third fixed ultrasonic frequency signal in the multiphase liquid; receiving a Doppler shifted third fixed frequency signal resulting from reflection from the gas bubbles and generating a fourth electrical signal in response thereto; and receiving the fourth electrical signal and the third fixed frequency signal and determining the signal strength of the Doppler shifted second fixed frequency signal from which the volume of the gas bubbles is determined.

Benefits and advantages of embodiments of the present invention include, but are not limited to, providing a system and method for noninvasively measuring chosen parameters of a multiphase fluid, wherein the measurements are independent of each other, and are sufficient to derive all necessary information.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 11A illustrates a measurement where the same disturbance is detected by both channels, but shifted in time, while

FIG. 13B illustrates the corresponding Fast Fourier Transform (FFT) of the oscillation, while

DETAILED DESCRIPTION OF THE INVENTION

Briefly, the present invention includes a measurement system and method for permitting multiple independent measurements of several physical parameters of multiphase fluids flowing through pipes. Multiple sensors are placed in acoustic communication with or attached to the outside surface of a section of existing spool (metal pipe), typically less than 3 feet in length, for noninvasive measurements. Sound speed, sound attenuation, fluid density, fluid flow, container wall resonance characteristics, temperature for oil-cut correction, and Doppler measurements for gas volume fraction may be simultaneously measured by the system. In what follows, a multiphase fluid may include at least one liquid component and at least one gaseous component, the at least one liquid component including liquid hydrocarbons, oil and water, and the gaseous component including a gaseous hydrocarbon.

The elements of the present apparatus and method function synergistically as follows:

1. Liquid flow is measured using a dual channel sound transmission correlation. When there is a large amount of fluctuation present in the flow stream due to turbulence of gas bubbles, the dual channel transmission signal becomes erratic, but the chirp transmission signal clearly shows an interruption of transmission which may be taken into account. Further, the chirp measurement is done very rapidly (about 100 µs per measurement), whereas the flow measurement takes significantly longer.
2. To determine the flow, the operating transmission frequency is chosen such that there is maximum sound transmission through the appropriate wall resonances. Although information regarding this can be derived from the chirp transmission data, it is more accurate and reliable to do a slow sweep of the data (several seconds) to obtain the wall resonance information as this measurement shows more detailed structures in the wall peak. Because of the longer measurement, time fluctuations due to flow are averaged out and the wall resonance information is clearly observed. The sweep measurement is done in the frequency domain by sweeping a frequency through the transmitter and recording the sound transmission amplitude (and phase) as a function of frequency.
3. Doppler measurements for gas volume and the chirp transmission measurements are also correlated, and these two measurements may be compared to obtain a reliable value of the gas volume.
4. The liquid density measurements combine the frequency sweep method with the Doppler transducers to obtain the results. The same situation exists for liquid viscosity determinations. This information is then correlated with the sound attenuation measurement through the chirp transmission as liquid viscosity and its sound attenuation are related.

Figure 1A:
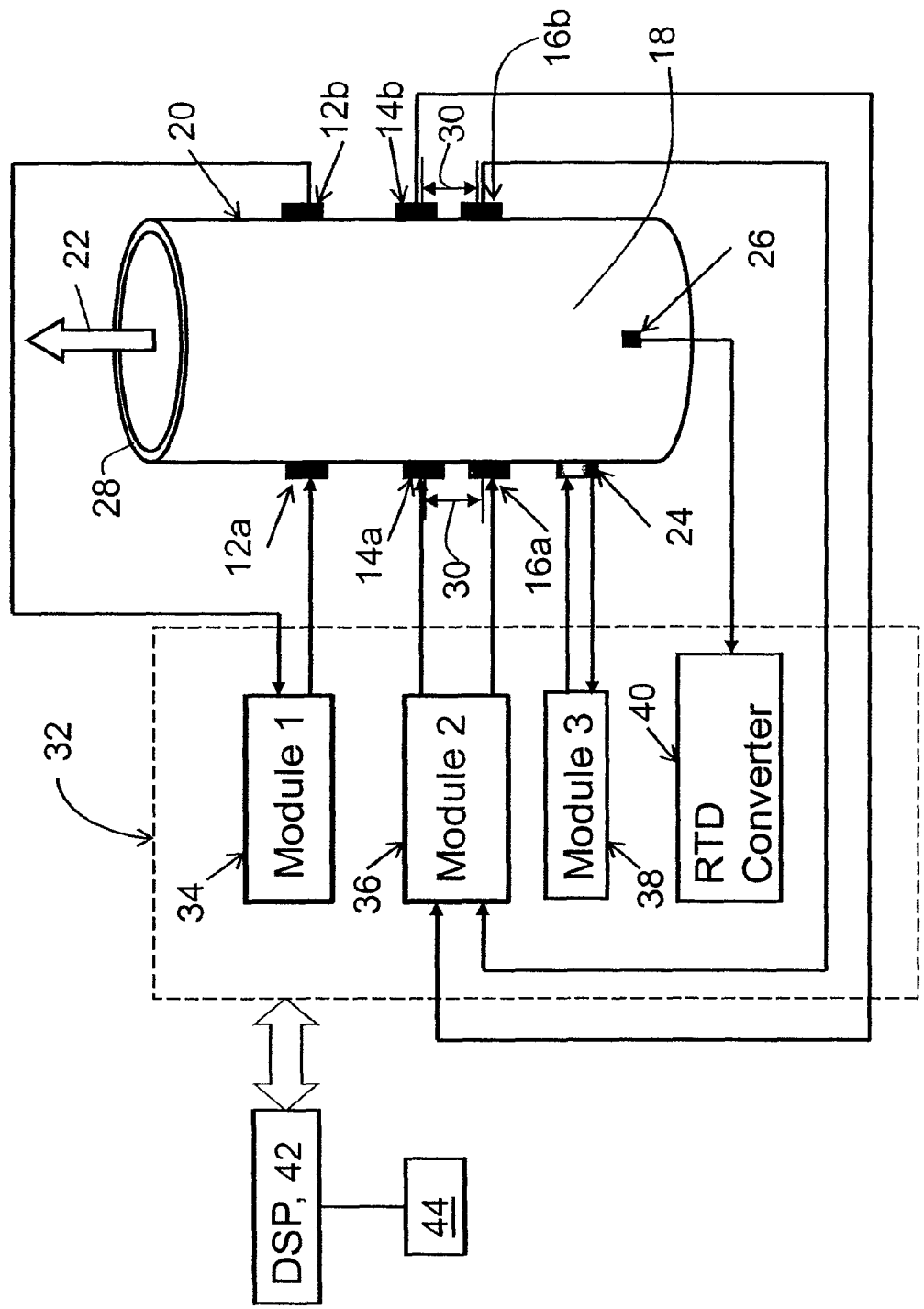
FIG. 1A is a schematic representation of an embodiment of the measurement system of the present invention.

Reference will now be made in detail to the present embodiments of the invention, examples of which are illustrated in the accompanying drawings. In the FIGURES, similar structure will be identified using identical reference characters. It will be understood that the FIGURES are for the purpose of describing particular embodiments of the invention and are not intended to limit the invention thereto. Turning now to FIG. 1A, a schematic representation of an embodiment of the measurement system, 10, of the present invention is shown. Three pairs of piezoelectric transducers, 12a, 12b, 14a, 14b, 16a, and, 16b, is placed in ultrasonic communication with or attached, using glue, as an example, to outer surface, 18, of pipe, 20, which may be part of the existing pipe structure, through which multiphase fluid, 22, is flowing. Each transducer in each pair of transducers 12a and 12b, 13a, and 13b, and 14a, and 14b, is positioned on outer surface 18 of pipe 20 each member of each pair of transducers being diametrically opposed to the corresponding second member in that pair. A fourth transducer, 24, is a dual-element transducer in which one element functions as the transmitter and the other as receiver, is placed in ultrasonic communication with or attached to outer surface 18 of pipe 20, at substantially the same radial position on pipe 20 as the three pairs of piezoelectric transducers. For convenience, the transducers may be attached to a spool (a section of a pipe) that is inserted in the measurement pipeline, effectively becoming part of the original pipeline. All transducers are attached on the outside surface of the pipe, and all measurements are made in a noninvasive manner.

Temperature sensor, 26, is attached to outer surface 18 of pipe 20 for measuring the temperature of fluid 22 contacting pipe wall, 28. As an example, transducers 12a and 12b may be utilized to measure sound speed and attenuation using frequency chirp excitation. Continuing the example, transducers 14a and 14b, and 16a and 16b are disposed such that the two pairs are parallel and separated by a chosen distance, 30, along pipe 20, and may be used for acoustic flow measurements. Chosen distance 30 may be between about one and approximately two outer pipe diameters. One of the pairs of transducers may also be used for slow frequency sweep measurements to determine the resonance peaks in wall 22 that are needed for the flow measurement. Dual-element transducer 24 may be used for ultrasonic Doppler measurements, for detecting gas, for determining gas volume in conjunction with the flow measurement, and for liquid density measurements.

Electronic circuitry, 32, for operating the apparatus described hereinabove includes three identical modules, 34, 36, and, 38, the modules and circuitry being advantageously interchangeable, and resistance temperature detector converter (RTD) for converting the signal from temperature sensor 26, for example, a platinum resistance thermometer (PRT) to digital form. Electronic circuitry 32 is controlled by digital signal processor (DSP), 42, that is in turn controlled by computer, 44.

Figure 1B:
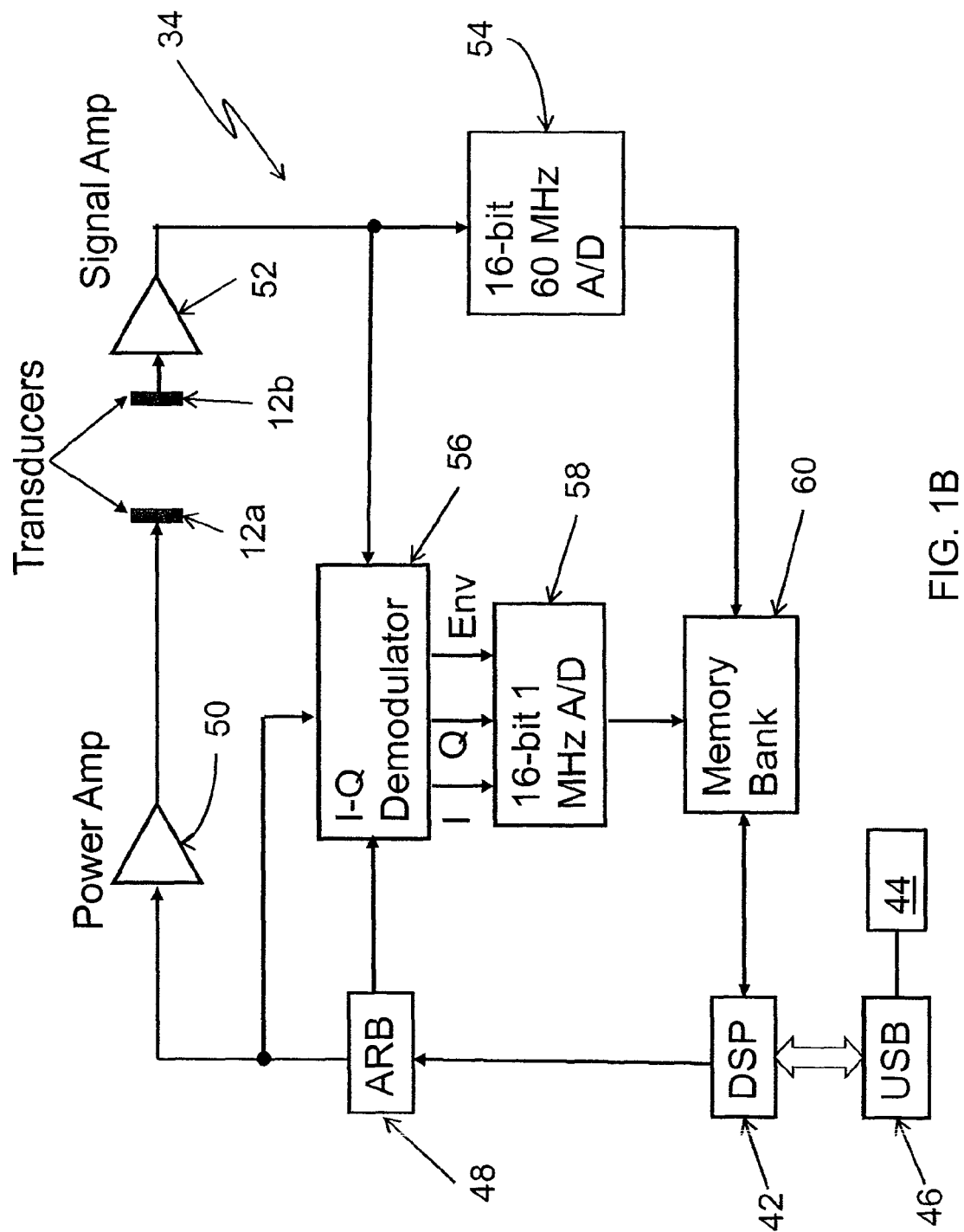
FIG. 1B is a schematic representation of an embodiment of one of the electronics modules.
Figure 1C:
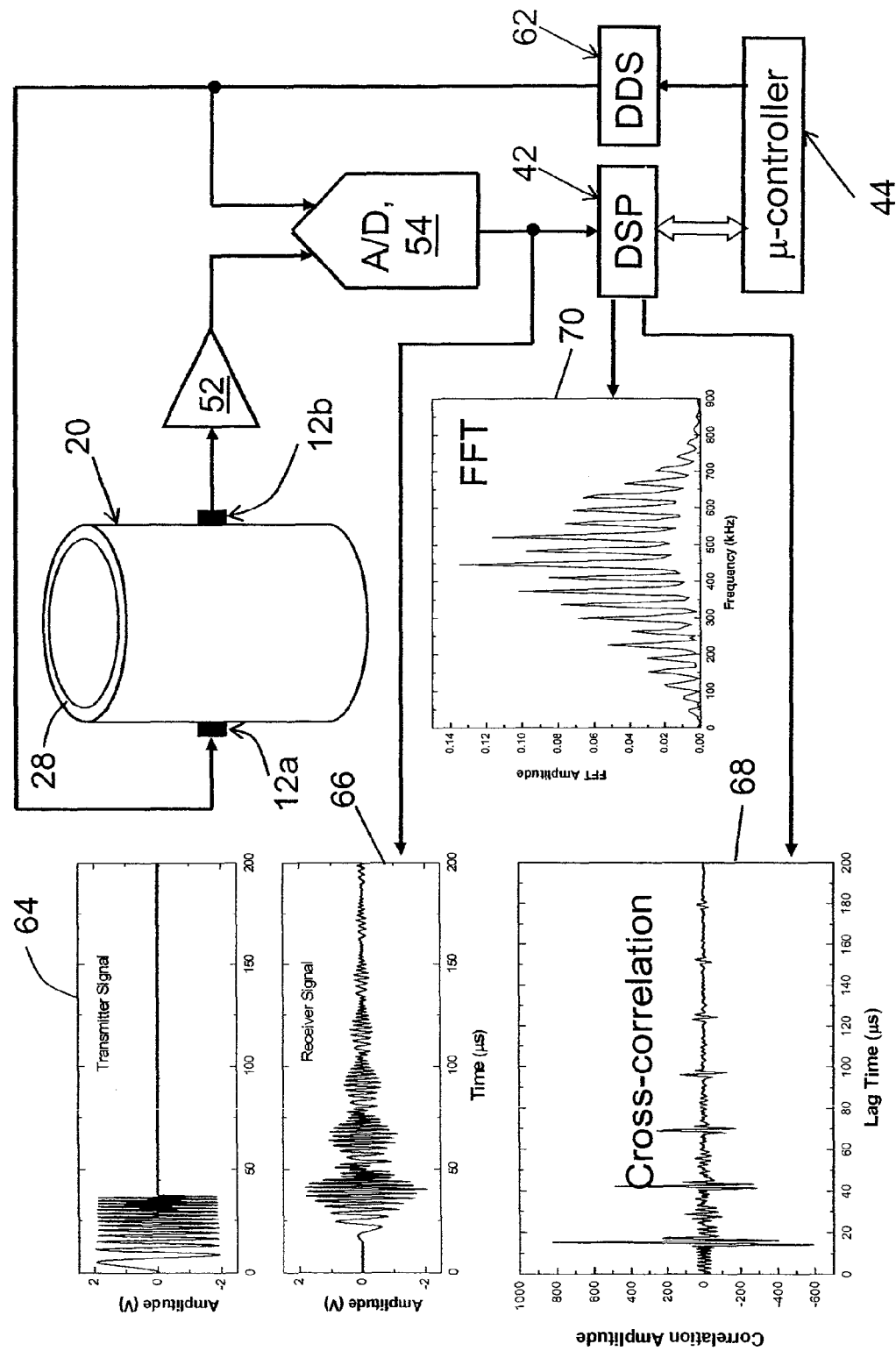
FIG. 1C is a schematic representation of an apparatus for generating frequency chirp signals and processing the data using cross-correlation, Fast Fourier Transformations (FFT), and other signal processing functions.

Referring to FIG. 1B, an embodiment of module 34 is shown. Computer 44 may be an external computer, which drives DSP 42 through USB port 46 for communication. DSP 42 controls arbitrary waveform generator (ARB), 48, which is capable of generating waveforms having desired mathematical forms. For the measurements described hereinbelow, frequency chirps between 100 kHz and 10 MHz having Gaussian envelopes, fixed-frequency sine waves, and FM modulated signals are used. ARB 48 has two outputs that are 90° apart in phase. The in-phase signal is amplified by power amplifier, 50, and is applied to piezoelectric transmitter transducer 12a, while the quadrature (cosine wave) signal is directed to I-Q (in phase-quadrature) demodulator, 56. Typically, the transducer is grounded on one end. The excitation voltage may be as high as 50 V. However, occasionally, the grounded configuration can pick up ambient noise. To avoid this effect, the excitation signal may be applied differentially to the transducer by having the output from power amplifier 50 connected to an RF 1:1 ratio transformer, not shown in FIG. 1B, with transducer 12a being connected to this transformer, which electrically isolates transducer 12a, thereby avoiding spurious signal pick up. The signal received from transducer 12b is amplified by a low noise signal amplifier, 52, having controllable gain (up to 70 dB) and is directed to either a high speed (60 M samples/s) 16-bit analog-to-digital (A/D) converter, 54, for chirp measurements, or to I-Q quadrature demodulator, 56, for flow and Doppler measurements. The output of I-Q demodulator 56 provides three signals (two quadrature signals: real and imaginary, and the signal envelope (ENV)). The envelope signal is determined using a 10 MHz bandwidth rms-to-dc converter circuit, not shown in FIG. 1B. This envelope signal can also be determined from the real and imaginary output signal as well, but the envelope detector circuit is convenient for observing fast changes in signal amplitude. These data are digitized by 16-bit 1 M samples/s A/D converter, 58. All the digitized data are stored in high-speed memory bank, 60, and analyzed by DSP 42, which can perform cross-correlation, Fast Fourier Transformations (FFT) and other signal processing functions, are shown in FIG. 1C, with direct digital synthesizer, 62, taking the place of ARB 48, as will be described in more detail hereinbelow.

A. Measurement of Fluid Composition:

In a 2-phase fluid, for example, an oil/water mixture, the sound speed and sound attenuation are related to the composition of the fluid. The sound speed is typically measured by a pulse-echo method where a sound pulse of certain duration created by an ultrasonic transducer (source, 12a in FIG. 1A) attached to the outer wall of the pipe is sent through a liquid and is detected on the opposite side of the pipe with a second transducer (receiver, 12b in FIG. 1A). If the time of flight of the pulse is determined, the sound speed can be calculated from this time and the distance between the sound source and sound receiver. Such measurement can also be made with a single transducer that operates both as a transmitter and the receiver, such as dual transducer 24 in FIG. 1A. A tone burst, where a predetermined number of cycles, for example, ten, of a fixed frequency is directed into the fluid, may be used instead of a pulse. Measurements at various frequencies, one frequency at a time, may be made but the time-of-flight determination is more difficult because identification of the actual start of the pulse in a fluctuating sound transmission environment of a flowing multiphase liquid is difficult. To improve the quality of the signal, it is quite common to further process the raw signal. The signal-to-noise ratio (S/N) of the processed signal to the signal-to-noise ratio of the unprocessed signal is given by the Process Gain as:

Process Gain=Frequency Bandwidth×Time Duration.

In the case of a pulse, the time duration is very short, whereas in the case of a single frequency tone burst the frequency bandwidth is extremely small. In either case, the process gain is small and introduces a large amount of noise in the measurement, thereby requiring signal averaging and additional measurement time. These techniques are unsuited for real-time measurements, although they are used extensively in industry. There are additional difficulties introduced by the presence of a pipe or container wall which makes these techniques difficult to use for noninvasive measurements. A pulse will ring in the wall due to multiple reflections within the wall thickness, which makes time-of-flight determinations difficult. Similarly for tone burst measurements. The Swept Frequency Acoustic Interferometry (SFAI) technique developed by Dipen N. Sinha in U.S. Pat. No. 5,767,407, overcomes the S/N ratio problem by using a broad frequency sweep measurement over a long duration, which permits accurate sound speed and sound attenuation measurements to be made in static fluids. However, this approach has the limitation that if the measurement is made in a flowing system, such as multiphase fluid (oil/water/gas), an average value over a large volume of fluid flowing through a pipe is obtained because the volume of fluid being measured has passed the effective measurement zone of the transducers during the longer-duration sweep measurements, typically several seconds.

Orders of magnitude improvement in signal-to-noise ratio may be obtained by using a broad bandwidth frequency sweep, for example, between about 100 kHz and approximately 10 MHz, but having a shorter duration, between approximately 10 μs and about 10 ms, which is commonly known as a frequency chirp signal. Returning to FIG. 1C, in an embodiment of the invention, frequency chirp signal, 64, was generated by direct digital synthesizer (DDS) 62 controlled by micro-controller 44 and applied to piezoelectric transducer (transmitter) 12a externally attached to the exterior surface 18 of liquid-filled metal pipe 20. Second transducer (receiver) 12b was attached diametrically opposite on the exterior surface 18 of pipe 20 to first transducer 12a, and aligned to intercept the sound beam generated by the transmitter. After amplification by amplifier 52, the received signal was digitized by analog-to-digital (A/D) converter 54. The received signal, 66, includes multiple reflections within the liquid path as the signal bounces between the opposite sides of the interior of the pipe wall. The effect of wall 28 is minimal since the pipe used had a thin wall. The transmitted signal was cross-correlated with the received signal, 68, in digital signal processor (DSP) 42 controlled by microcontroller 44. The first sharp peak indicates the time-of-flight of the signal from transducer 12a to receiver 12b. The sharpness of the peak is due to the high process gain as discussed hereinabove, and can readily be easily determined. Cross-correlation signal processing 68 is clearly a signification improvement over the received raw signal 66, thereby improving the measurement of sound speed.

The time measurement (time to the first peak in cross-correlation 68) includes the sound travel time through the walls of the container (negligible for the thin pipe wall of the present measurement), and is generally taken into consideration in the derivation of accurate fluid sound speed measurements. Subsequent peaks in cross-correlation 68 originating from multiple bounces within the opposite walls of the pipe may be used to obtain additional measurements of the sound speed. For example, the time difference between the second peak and the first peak, or any consecutive two peaks, is twice the time taken for the sound to travel in the fluid, and does not include any time expended in the pipe wall. Thus, for greater accuracy in the sound speed measurement, the time between all the observed peaks can be used since this provides multiple measurements which may be averaged.

Figure 2:
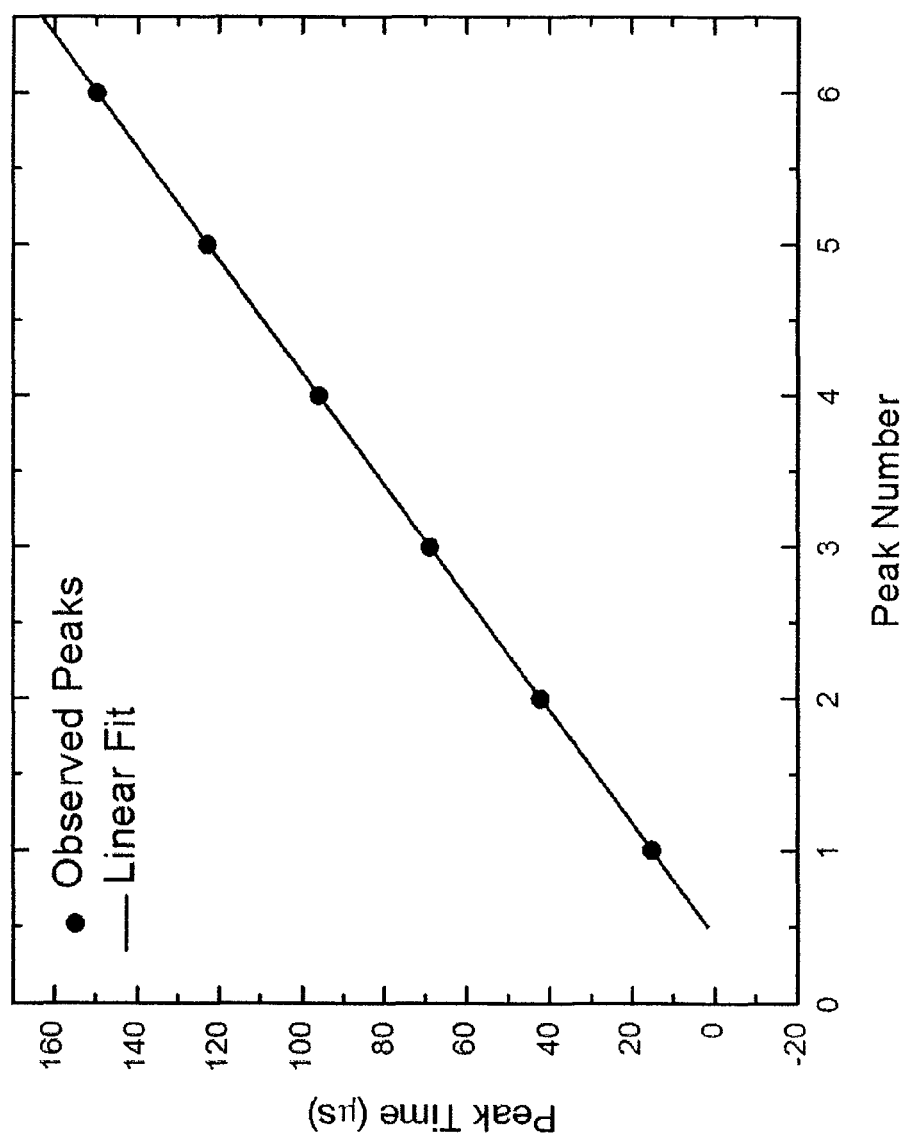
FIG. 2 shows the inclusion of subsequent echoes in the measurement of the speed of sound.

Another method for including subsequent echoes in the measurement of the speed of sound is shown in FIG. 2. The time for each peak is plotted against the peak index, where each echo is numbered. Each echo takes a finite time to bounce back and forth in the wall of the pipe between the inner and outer surfaces thereof, and through the liquid, which time is fixed for all echoes. Therefore, a linear least squares fit to the data provides the time-of-flight measurement as the slope. This is equivalent to determining the average time between each consecutive echo, but in a much simpler manner. In this situation, the path length is 2 cm, and the slope is 26.886 (correlation coefficient of fit=1.0), which corresponds to the round trip time through the pipe. This gives a sound speed of 1487.7 m/s for water, which compares well with the value given in the literature.

The above discussion shows how an accurate measurement of sound speed can be made using the frequency chirp method noninvasively and quickly. The entire measurement was carried out in less than 200 µs. For liquids that are rapidly flowing through a pipe the measurements can be easily made faster than 50 µs with good accuracy. This measurement time can be reduced to 10 µs in practice without significantly affecting the measurement accuracy, which is sufficiently rapid that for typical oil flows through pipes during pumping from downhole reservoirs, any small volume of liquid has moved less than 1 mm within the active zone between the transducers and an instantaneous measurement of sound speed may be obtained.

Another method for determining sound speed is to fast Fourier transform the received signal (or the cross-correlation signal) into the frequency domain, 70. This spectrum illustrates equally spaced peaks in frequency ($\Delta f$), which is directly related to the speed of sound: sound speed=2×liquid path length×$\Delta f$. The observed frequency spectrum reflects the bandwidth of the transducer used and shows an amplitude fall off on both sides of the center. Since the peak spacing is used in the speed of sound determination, and not the amplitude, this effect does not change the values obtained for the speed of sound. The value of $\Delta f$ measured from FIG. 1C is 37.45 kHz which results in a sound speed of 1486 m/s for water. These measurements were made in a 2 cm diameter, water-filled steel pipe having a 1 mm thick wall to illustrate the measurement.

The frequency spectrum method does not provide new information, but is often more readily handled than data obtained from time plots or correlation plots. With the frequency spectrum many peaks are available for determining the frequency spacing and a good average value may be obtained. In order to use the frequency spectrum method, there must be echoes present in the original recorded received transducer signal. Such echoes are created when standing waves (resonances) are formed in the fluid container cavity formed by the opposing walls of the container. Additional information concerning data analysis may be found in patent application Ser. No. 13/226,444 for "Method For Noninvasive Determination Of Acoustic Properties Of Fluids Inside Pipes", by Dipen N. Sinha et al. filed on 6 Sep. 2011, the entire contents of said patent application being hereby incorporated by reference herein for all that it discloses and teaches.

Figure 3:
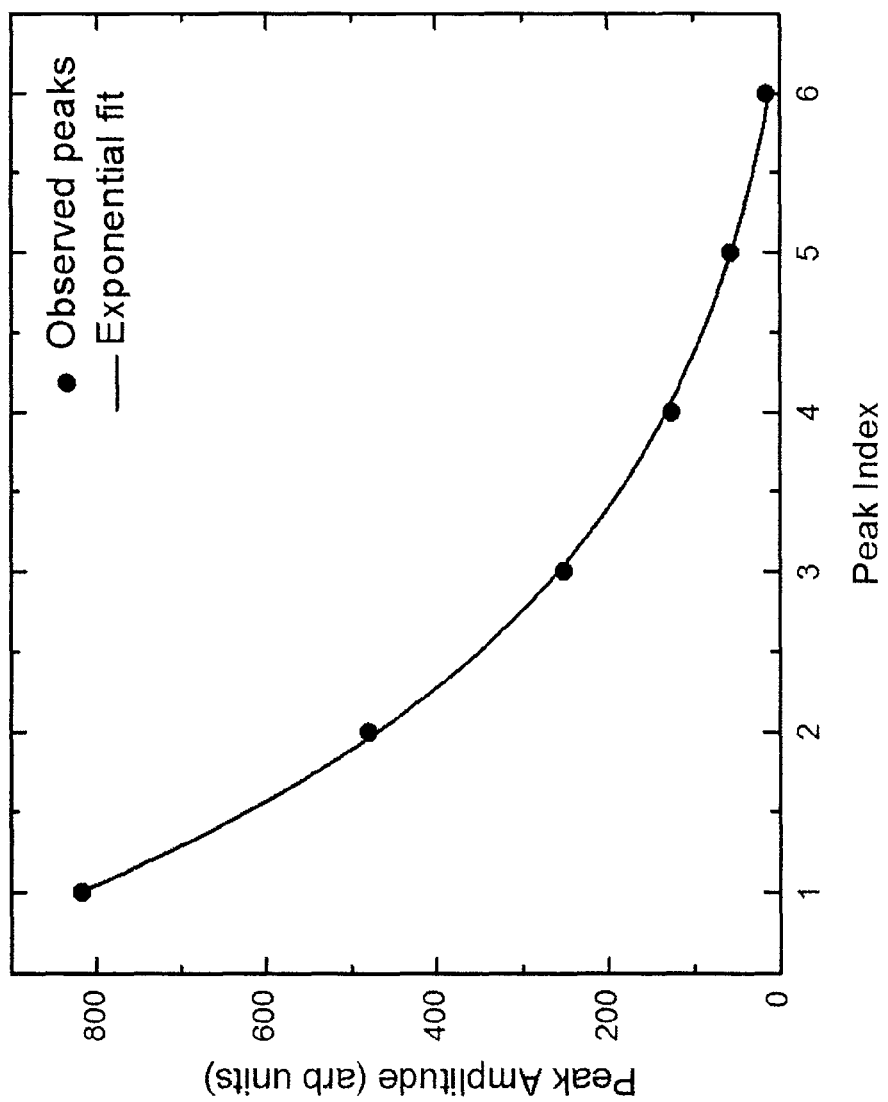
FIG. 3 shows the peak amplitudes as a function of peak index (solid circles), where the solid line is an exponential fit to the experimental data, from which the sound attenuation may be determined from the exponent used for the fit.

Sound attenuation in the liquid may also be determined from the frequency spectrum by measuring the peak width $\Delta f$ of each peak over the entire frequency range. This permits frequency dependent sound attenuation the fluid to be determined, which assists in the determination of liquid composition. An alternative approach is to determine the liquid attenuation from cross-correlation plot by observing the peak amplitude decay. FIG. 3 shows the peak amplitudes as a function of peak index (solid circles). The solid line is an exponential fit to the experimental data. Since the path length is known, the sound attenuation may be determined from the exponent used for the fit.

Figure 4:
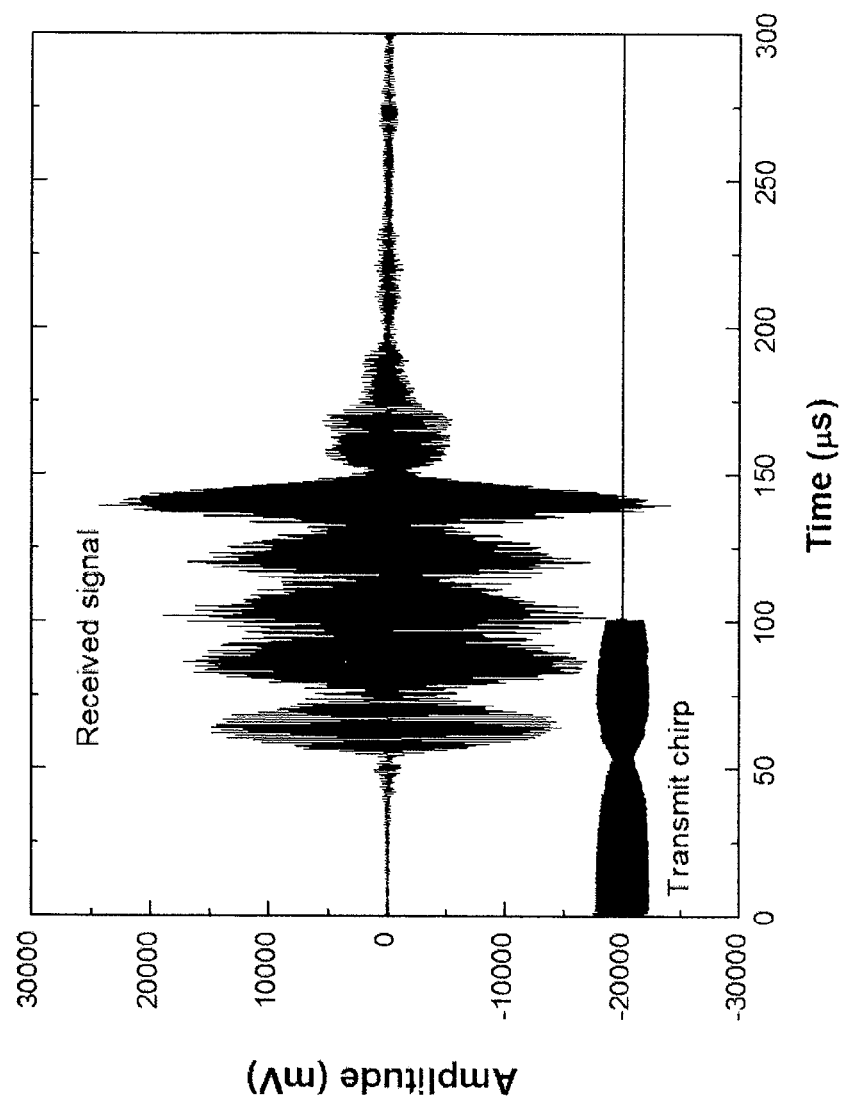
FIG. 4 shows a chirp measurement in a 3-inch diameter (ID) steel pipe with ¼ inch-thick wall through a mixture of oil and water in a 60-40 ratio using an apparatus similar to that shown in FIG. 1C hereof.

For pipes or containers having thick walls, multiple reflections or ringing in the wall thickness make time-of-flight measurements more difficult, and traditional methods do not provide accurate measurements. Ringing may be viewed as thickness mode resonances of the wall. FIG. 4 shows a typical chirp measurement in a 3-inch diameter (ID) steel pipe with ¼ inch-thick wall through a mixture of oil and water in a 60-40 ratio. The apparatus used to obtain this trace was similar to that shown in FIG. 1C hereof. The frequency range of the transmit chirp signal applied to the transmit transducer was between about 1 and about 4 MHz with duration of 100 µs, which is shown as translated along the ordinate for clarity; otherwise it is symmetric around zero. The slight dip in the amplitude in the middle of the chirp signal is due to transducer impedance loading. The received signal shows a delay of approximately 53 µs, because of the propagation time through the fluid inside the pipe. The received signal shows a strong amplitude modulation, which is due to the sound transmission characteristics of the wall of the pipe.

Figure 5:
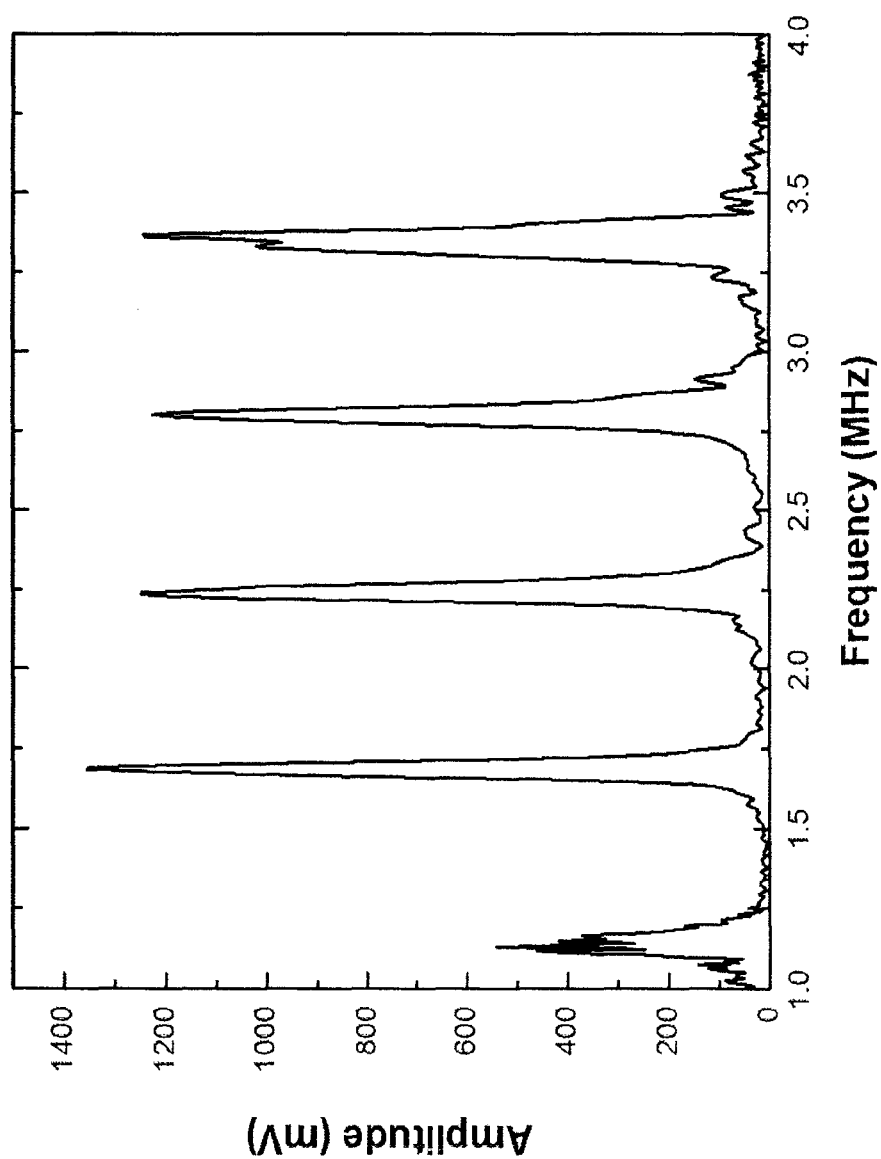
FIG. 5 shows the measured sound transmission of the wall as a function of frequency for the chirp signal illustrated in FIG. 4, hereof.

FIG. 5 shows the measured sound transmission of the wall as a function of frequency for the chirp signal illustrated in FIG. 4, hereof. As each of the wall thickness mode resonances in the sequence is matched in time by the frequency chirp signal, the transmitted signal reaches a maximum and subsequently diminishes, causing the modulation pattern observed. Such effects are present whenever noninvasive measurements through thick walls are performed. To determine the time-of-flight, one can take advantage the cross-correlation method described hereinabove. The cross-correlation of the received signal with the transmitted signal significantly improves the signal-to-noise ratio, as may be observed from FIG. 6. The time-of-flight is obtained from the first peak indicated by the arrow. Although echoes could only barely discernable from FIG. 5 hereof, cross-correlation signal processing extracts the echoes. Thus, the determination of accurate sound speed and sound attenuation using cross-correlation may be used for thick walls.

Figure 7:
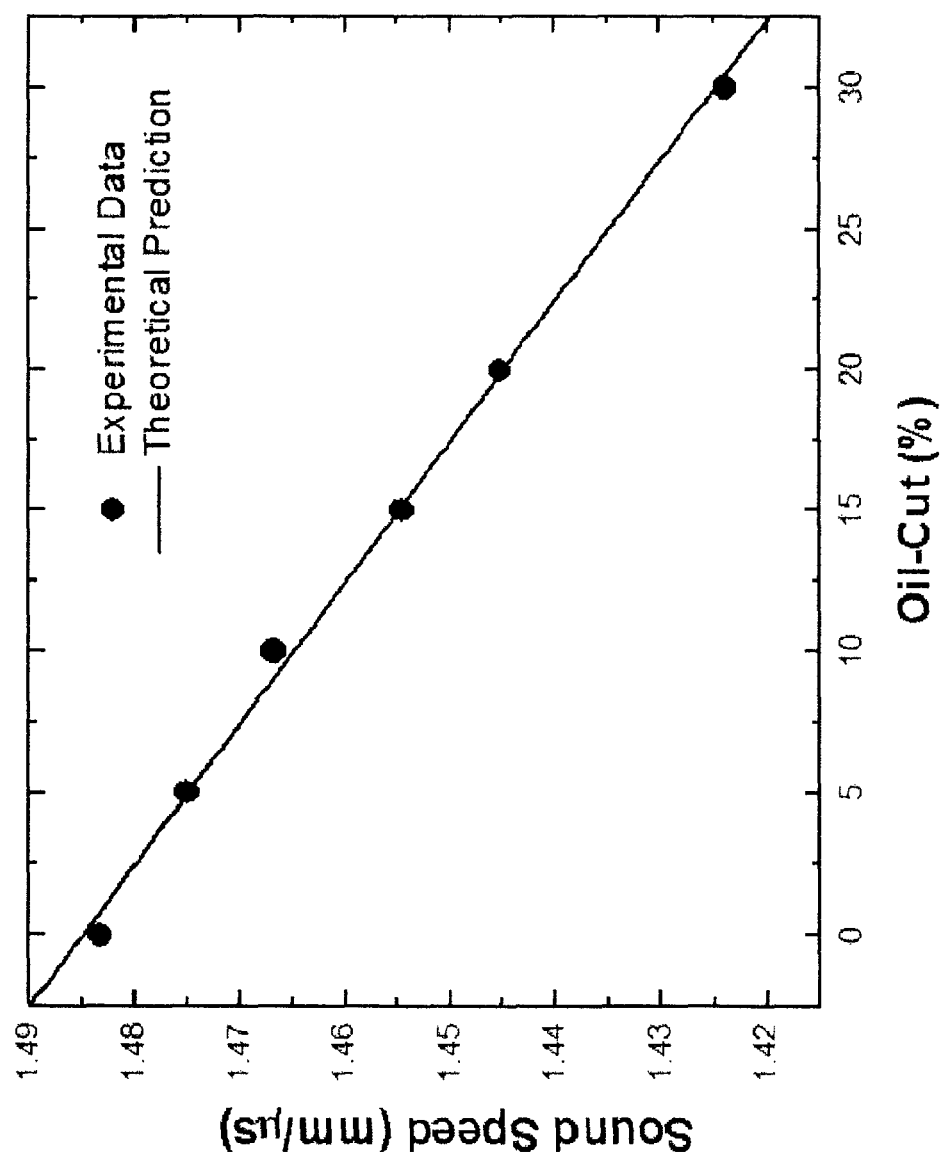
FIG. 7 shows data on the relationship between sound speed and oil-cut for a mixture of water and mineral oil.

For a 2-phase system, such as oil-water and little gas, sound speed and sound attenuation may be used for fluid composition determination. Sound attenuation is particularly valuable for high-water cut situation where there is small amount of water present. FIG. 7 shows data on the relationship between sound speed and oil-cut for a mixture of water and mineral oil. The sound speed of the mixture is related to the volume fraction of oil, $\phi$, according to the following:

$$\text{Speed}_{Mixture} = \phi \cdot \text{Speed}_{Oil} + (1-\phi) \cdot \text{Speed}_{Water}$$

This relationship provides a good representation of the actual measurement as shown in FIG. 7. The actual dependence depends on temperature since both sound speed and liquid density are affected by temperature. Typically, measuring the temperature dependence of sound speed and attenuation in samples of both 100% oil and 100% produced water provides an appropriate calibration for accurate composition determinations (3% accuracy) and, for high water-cut measurements, this accuracy may be as good as 0.1% since in high-water cut situations, the sound transmission is strong, and multiple echoes are readily detected, which allows more accurate determination of both sound speed and sound attenuation. This method is valuable for determining fluid composition when there is gas present in the liquid, although the amount of gas present should not be sufficiently large that there is no sound transmission through the fluid; for example, if the pipe were completely filled with gas and there were no liquid present.

Figure 8:
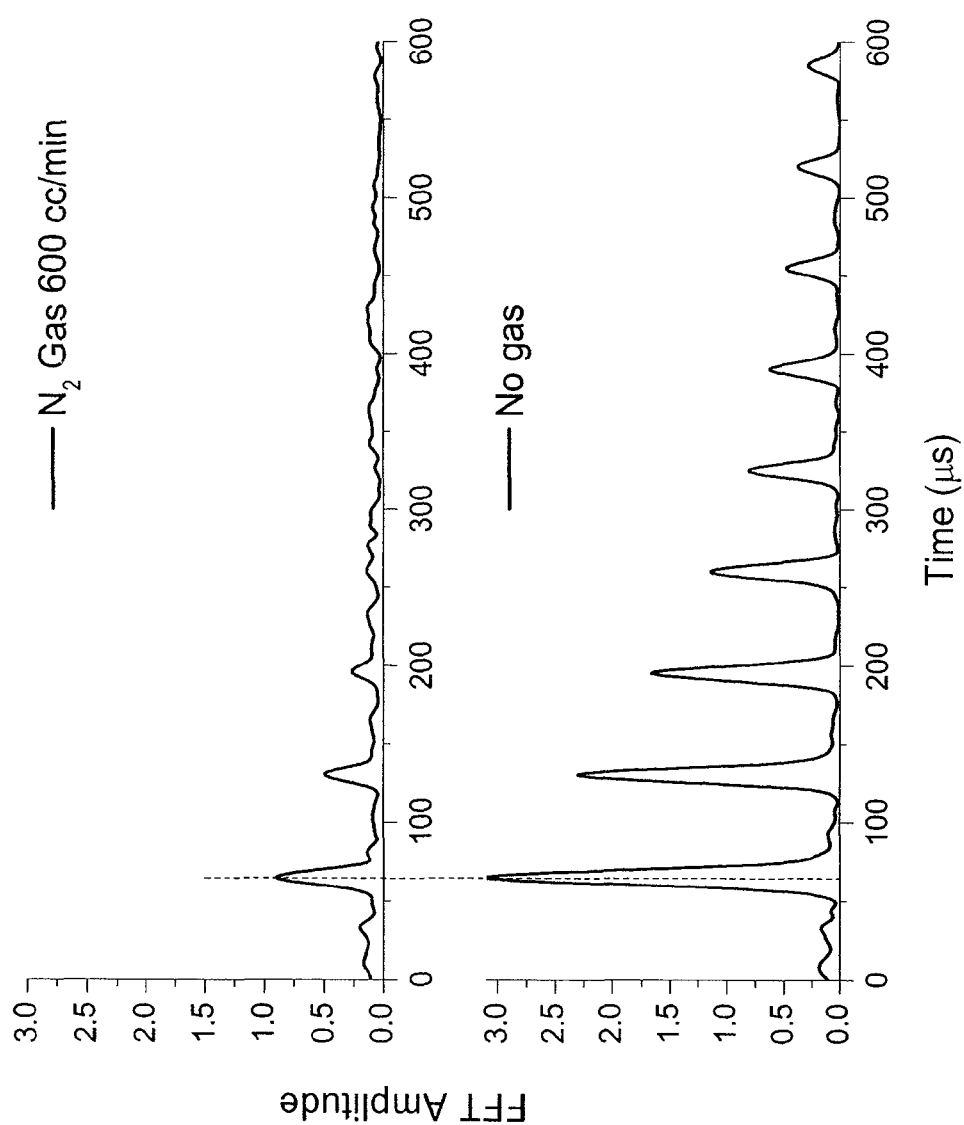
FIG. 8 shows the effect of gas flow during a measurement in water in a 3.7-in. diameter pipe, the bottom curve illustrating data obtained with water and no gas flow.

FIG. 8 shows the effect of gas flow during a measurement made in water in a 3.7-in. diameter pipe. The bottom part of FIG. 8 shows the data with water only, and no gas flow. The multiple echoes in the measurement in the cross-correlation plot where the y-axis is the envelope of the correlation amplitude may readily be observed. The data shown represent an average of 10 measurements. The upper part of FIG. 8 illustrates a measurement with nitrogen gas flowing at a rate of 650 cc/min through a 2 in. diameter steel pipe. These measurements were also repeated in a 3 in. diameter pipe with an oil/water composition of 90% water and 10% crude oil, with similar results. The principal effect is the diminished signal amplitude and a fewer number of echoes, as the sound is scattered by the gas bubbles. However, the time-of-flight remains unchanged, as may be observed from the vertical dashed line in FIG. 8. Therefore, the sound speed and, consequently, the fluid composition can be determined as described hereinabove. In a typical oil/water flow in an oil producing well, unless the well is a heavy gas producer, the flow is in the bubbly flow regime where small bubbles are flowing through the well. Often these wells use a static mixer to break up large bubbles or volumes of gas. During a typical acoustic measurement, the path between the pairs of transmitter/receiver transducers is not always completely blocked by bubbles as they are flowing through the well, and therefore if the measurements are averaged, the results do not show detrimental effects due to the presence of gas below a certain volume fraction of approximately 40% by volume. The time-of-flight changes when the fluid composition changes and not as the result of the presence of gas, if the gas volume is moderate. The measurement quality improves if multiple chirps are rapidly sequentially applied and the received signals are averaged. The apparatus described hereinabove permits such rapid fire signal averaging. For example, the data from 10 chirps may be averaged in the DSP in less than 2 ms. Gas volume determination will be discussed below.

Figure 6:
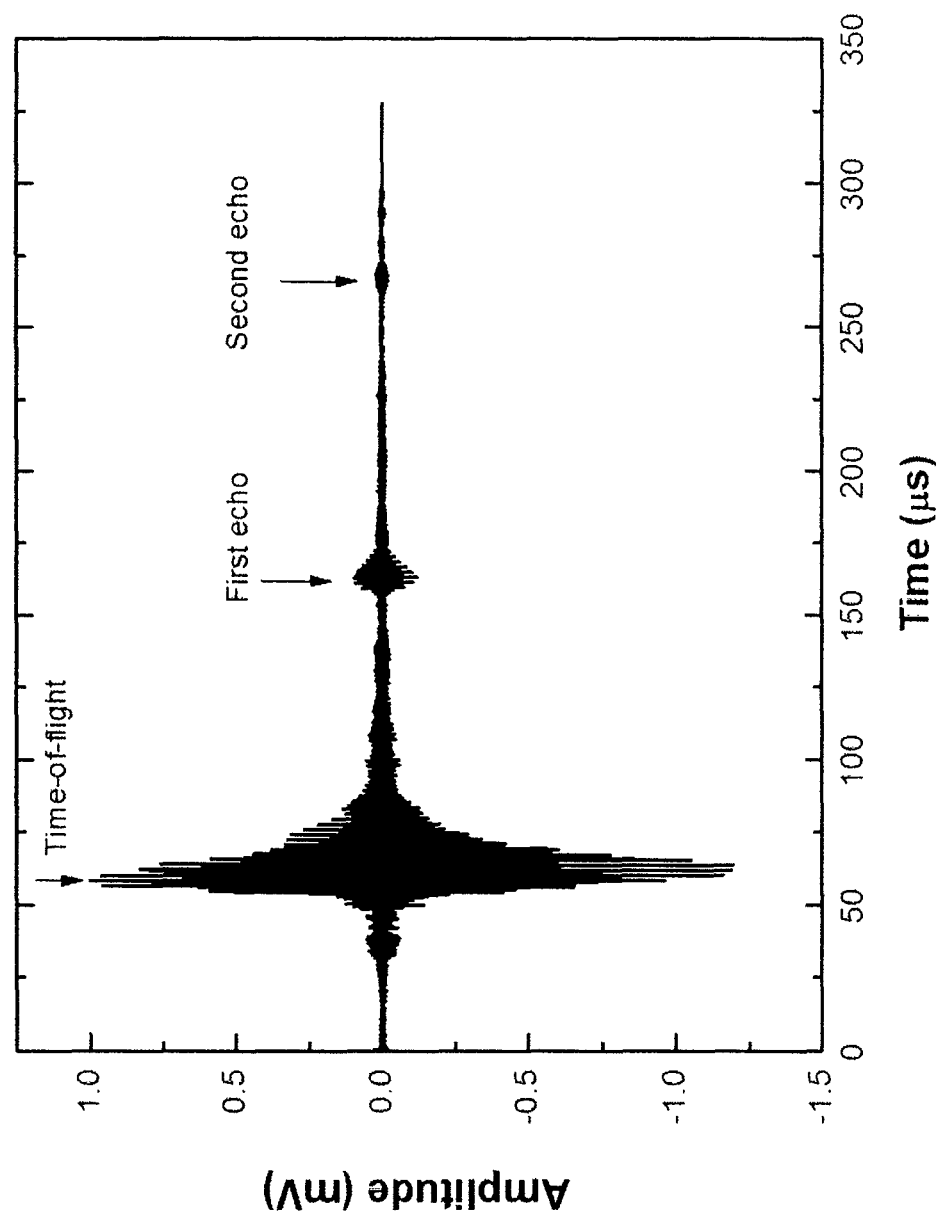
FIG. 6 shows the cross-correlation of the received signal of FIG. 5 hereof and the transmitted signal of FIG. 4 hereof, which significantly improves the signal-to-noise ratio.

B. Determination of Liquid Density:

The envelopes of the correlation signals of FIG. 6 hereof appear asymmetric with longer tails and faster rise times. This is due to multiple reflections within the wall as discussed hereinabove. The decay shapes contain information concerning the sound transmission through a solid-liquid interface and, consequently, to the acoustic impedance mismatch between the wall and the liquid inside the container (pipe). Since the container material is known and the sound speed of the liquid can be determined from the cross-correlation, the only unknown is the liquid density. With each reflection at the interface, the transmitted signal is observed to decrease in amplitude; the envelope of the decay of the correlation signal therefore provides information concerning the liquid density, which is the time-domain density determination.

An easier approach for monitoring liquid density is analysis in the frequency domain. This method is advantageous when the fluid inside the pipe does not permit any or much sound transmission, which occurs for high oil-cuts and large diameter pipes. The method takes advantage of the liquid in direct contact with the pipe wall, and it does not require sound transmission to the opposite side of the pipe. Either a dual-element transducer or a single transducer may be used on one side of the pipe. In the case of a dual-element transducer, one element is used as a transmitter and the other element as the receiver. Typically, standard Doppler transducers work well for this purpose, wherein the electronic circuits employed are illustrated in FIG. 1C. Another approach is to measure the electrical impedance of the single transducer. In either case, the amplitude of one of the wall resonance peaks (see FIG. 5) is monitored. The measurement is made by a frequency sweep (Frequency modulation), where the frequency is varied over a small frequency range that encompasses the resonance peak. The envelope of the response is recorded. The sound through the wall leaks out into the liquid, with the quantity of leakage depending on the acoustic impedance (Z=density×sound speed) mismatch between the wall material and the liquid. This affects the standing waves generated within the wall thickness since the waves traveling in one direction only partially interfere with the reflected waves, which in turn affects the amplitude of the resonance peak. In the situation where air or gas is present in the pipe, most of the signal is trapped in the wall and the resonance peak has the largest amplitude. However, as the liquid acoustic impedance increases and approaches that of the wall material, the resonance peak amplitude decreases according to the reflection coefficient (R) of the interface, and is given by:

$$R = \left[\frac{Z_2 - Z_1}{Z_2 - Z_1}\right]^2,$$

where $Z_2$ is the impedance of the fluid, and $Z_1$ is the impedance of the wall material.

Figure 9:
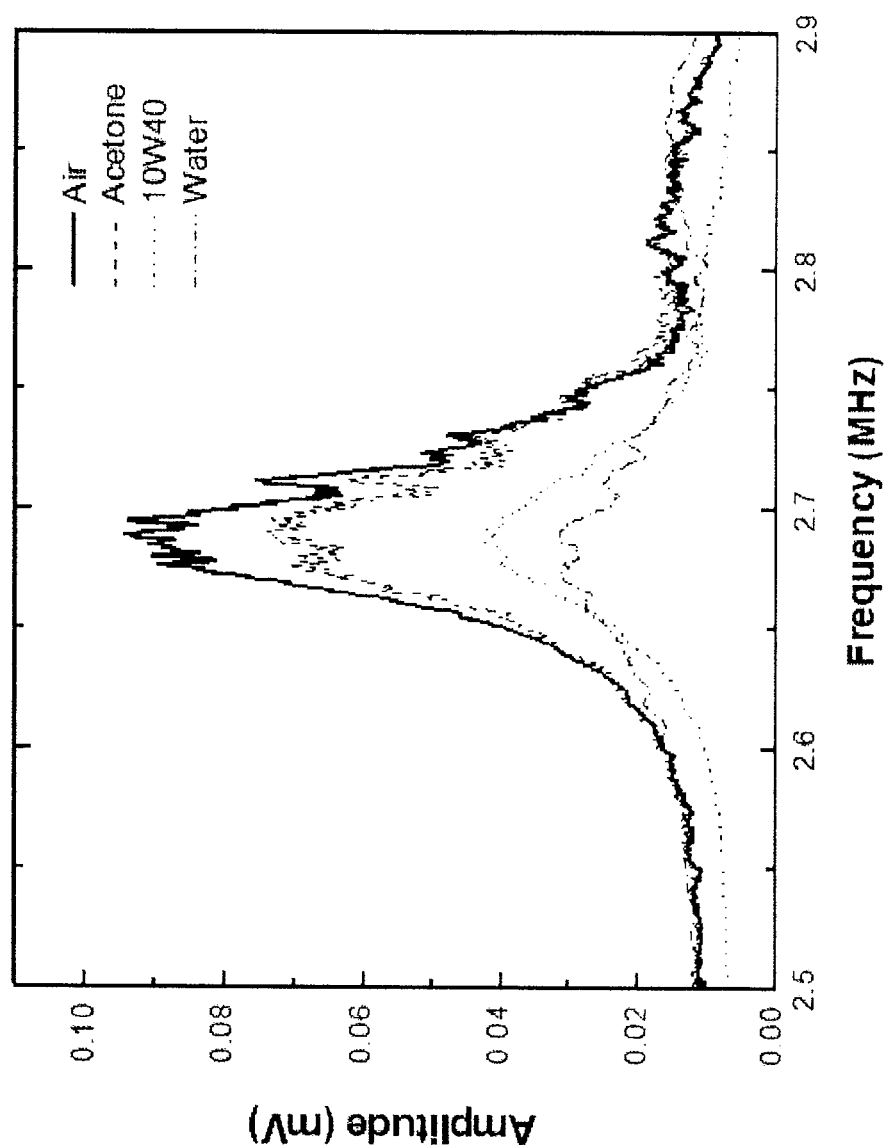
FIG. 9 illustrates the effect fluid density effect on the peak amplitudes of wall resonances made in an aluminum pipe with a 5 mm thick wall and containing acetone, water, and 10W-40 motor oil having densities of 0.79, 1.00, and 0.87 g/cm$^3$, respectively.

FIG. 9 illustrates measurements of the fluid density effect on the wall resonance peak amplitude made in an aluminum pipe having a 5 mm thick wall and containing acetone, water, and 10W-40 motor oil having densities of 0.79, 1.00, and 0.87 g/cm$^3$, respectively. Since the sound speed is determined independently by the methods described hereinabove, the liquid density can be determined from the peak height of the resonance. Fitting the resonance curve with a Lorentzian curve smoothes out the data and more accurate density measurements may be obtained. Liquid density measurements may be made in real time and in flowing liquids with an accuracy of less than 0.1 g/cm$^3$.

C. Determination of Liquid Viscosity:

The viscosity of the liquid may also be determined from these measurements since the fluctuations in the resonance curves of FIG. 9 significantly damp out when the viscosity of the liquid is high, as may be observed for 10W-40 motor oil. Glycerin (not shown in FIG. 9) smoothes out the data even more. Such fluctuations occur because there are always some guided waves generated in the pipe at the transducer/pipe interface, and these waves propagate circumferentially around the pipe and interfere to produce a standing wave pattern that is detected as and appears as ripples. The viscosity of the liquid causes such ripples to damp out, and smoother curves are observed as the viscosity increases.

Figure 10:
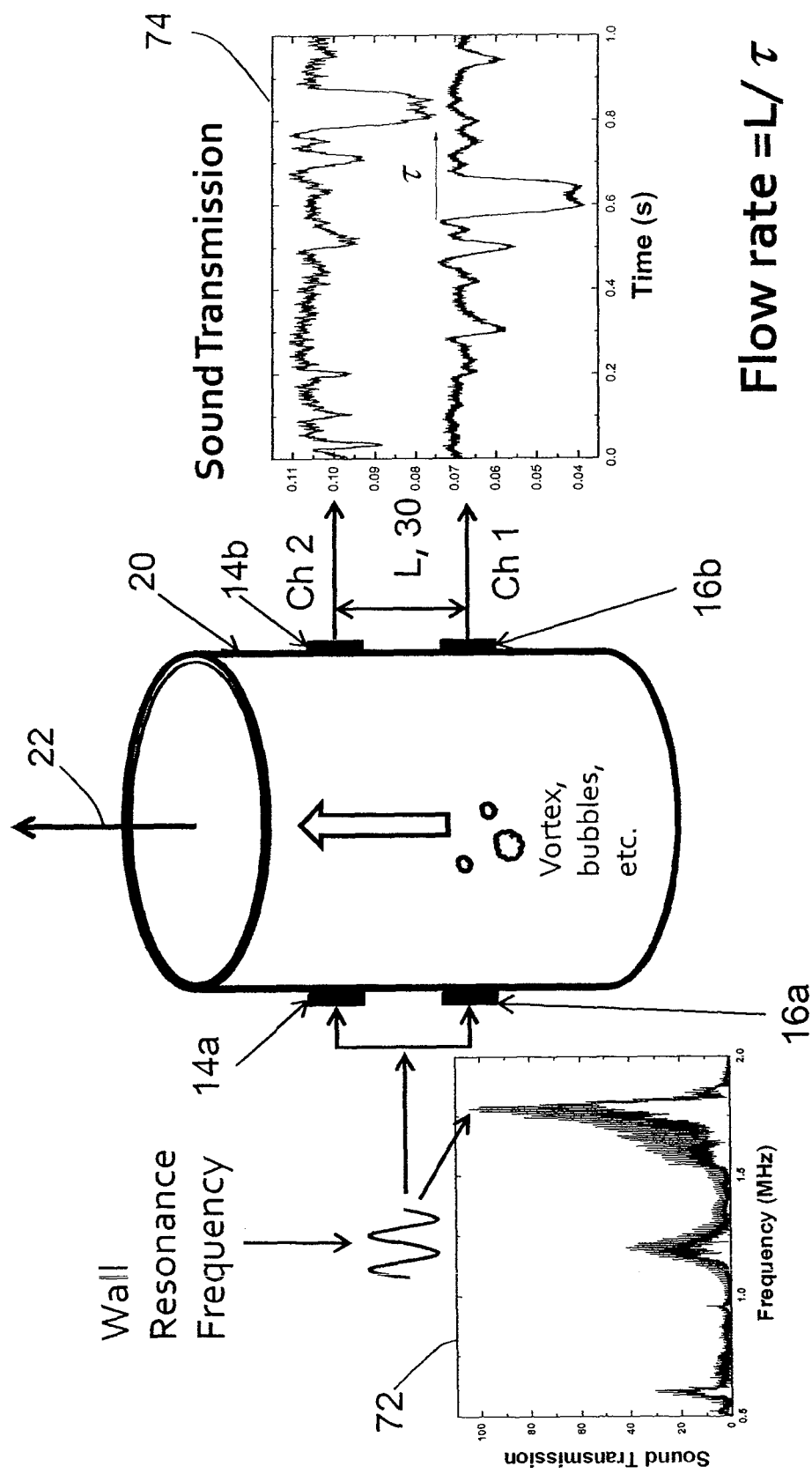
FIG. 10 illustrates apparatus for measuring fluid flow rate obtained when the distance between the two measurement locations is known and the time it takes for a disturbance to travel this distance is acoustically measured, assuming that the disturbance is essentially embedded in the fluid and travels with the fluid, the apparatus, which is part of the system illustrated in FIG. 1A hereof, including two pairs of transducers having a separation distance L.

D. Determination of Liquid Flow Rate:

Flow measurements rely on the fact that for any disturbance, such as bubbles or vortices, small density fluctuations in the liquid, and other localized inhomogeneities formed in a flowing fluid inside a pipe maintain their coherence for at least one pipe diameter. Therefore, if a localized disturbance is measured at two different locations in the pipe along the direction of the flow, correlations between the two should be observable. Accurate measurements of fluid flow rate may be obtained when the distance between the two measurement locations is known and the time it takes the disturbance to travel this distance is measured, assuming that the disturbance is essentially embedded in the fluid and travels with the fluid. The disturbance is acoustically monitored in an apparatus including two pairs of transducers 14a and 14b, and 16a and 16b, having a separation distance L, 30, and arranged on pipe 20 as illustrated in FIG. 10, which is a part of the system illustrated in FIG. 1A. Both transmitter transducers are excited by a fixed frequency of sound. As shown in inset, 72, a frequency corresponding to one of the resonance modes of the pipe wall may be selected, where the sound transmission is at a maximum.

The received signal from both channels is fed to the electronics package (FIG. 1A) where the envelope of the sound transmission is determined. Inset, 74, illustrates a typical measurement where the same disturbance is detected by both channels but shifted in time. Signals may be noisy with the coherent features embedded in the noise. The time delay may be determined using cross-correlation of the data, which may be performed in real time by DSP 42 (FIG. 1A) in the electronics package.

Figure 11A:
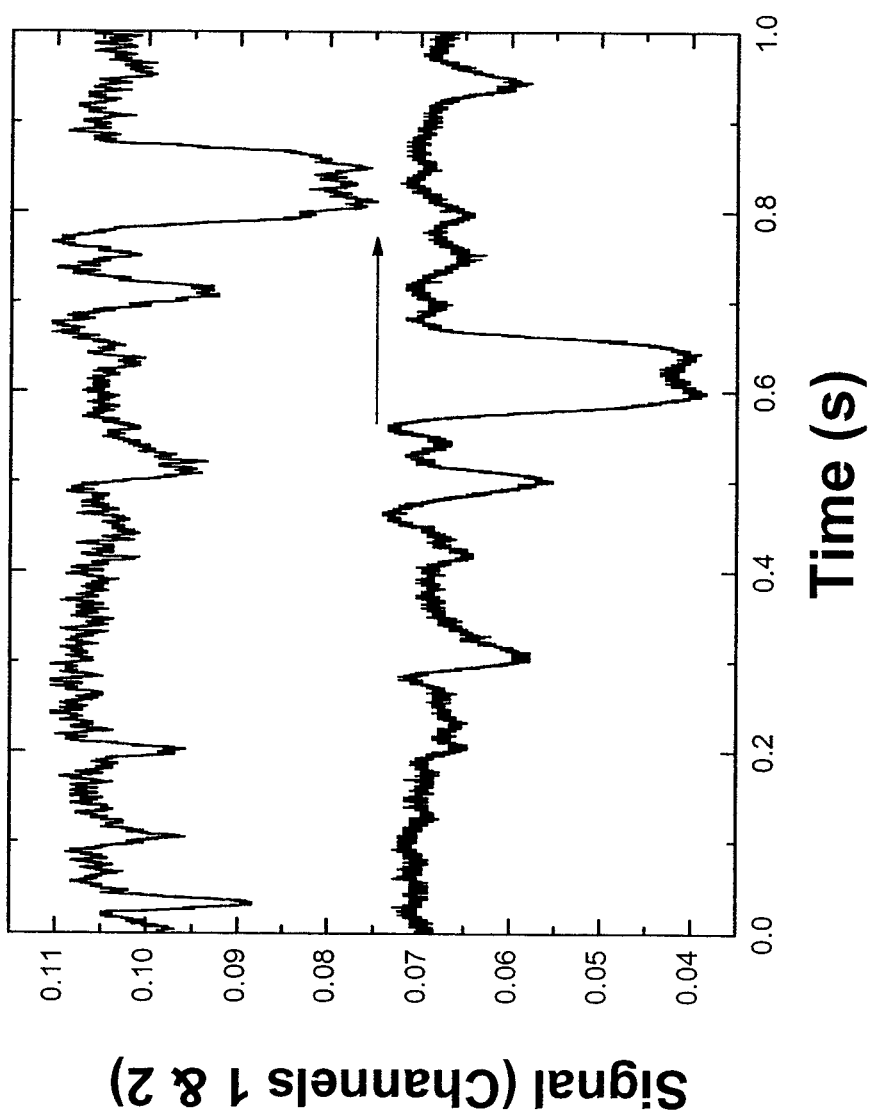
Figure 11B:
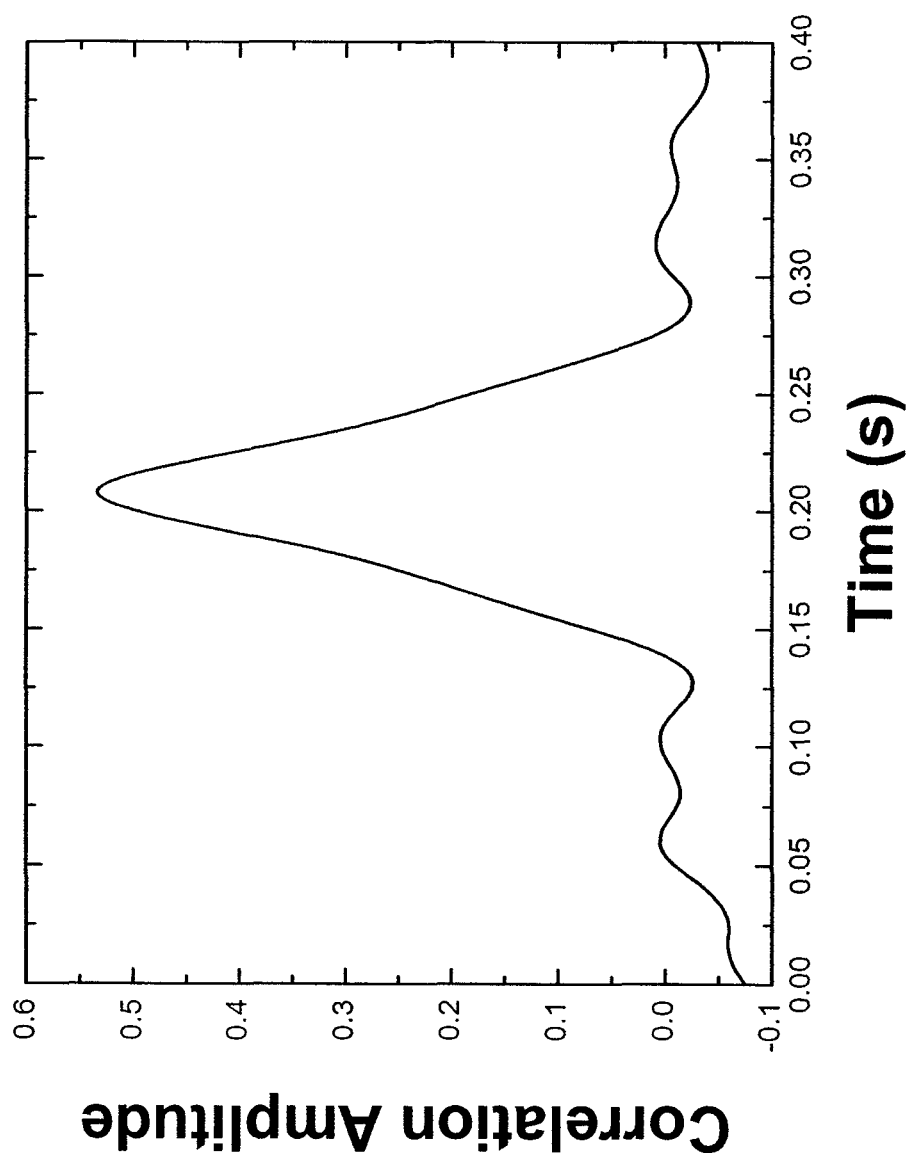
FIG. 11B shows the cross-correlation of the two channels which shows a peak that corresponds to the delay time, $\tau$ from which the flow speed may be calculated as $L/\tau$.

FIG. 11A shows an expanded inset 74 of FIG. 10, illustrating a typical measurement where the same disturbance is detected by both channels, but shifted in time, while FIG. 11B shows the cross-correlation of the two channels which illustrates a peak that corresponds to the delay time, τ, from which the flow speed may be calculated as L/τ.

Figure 12:
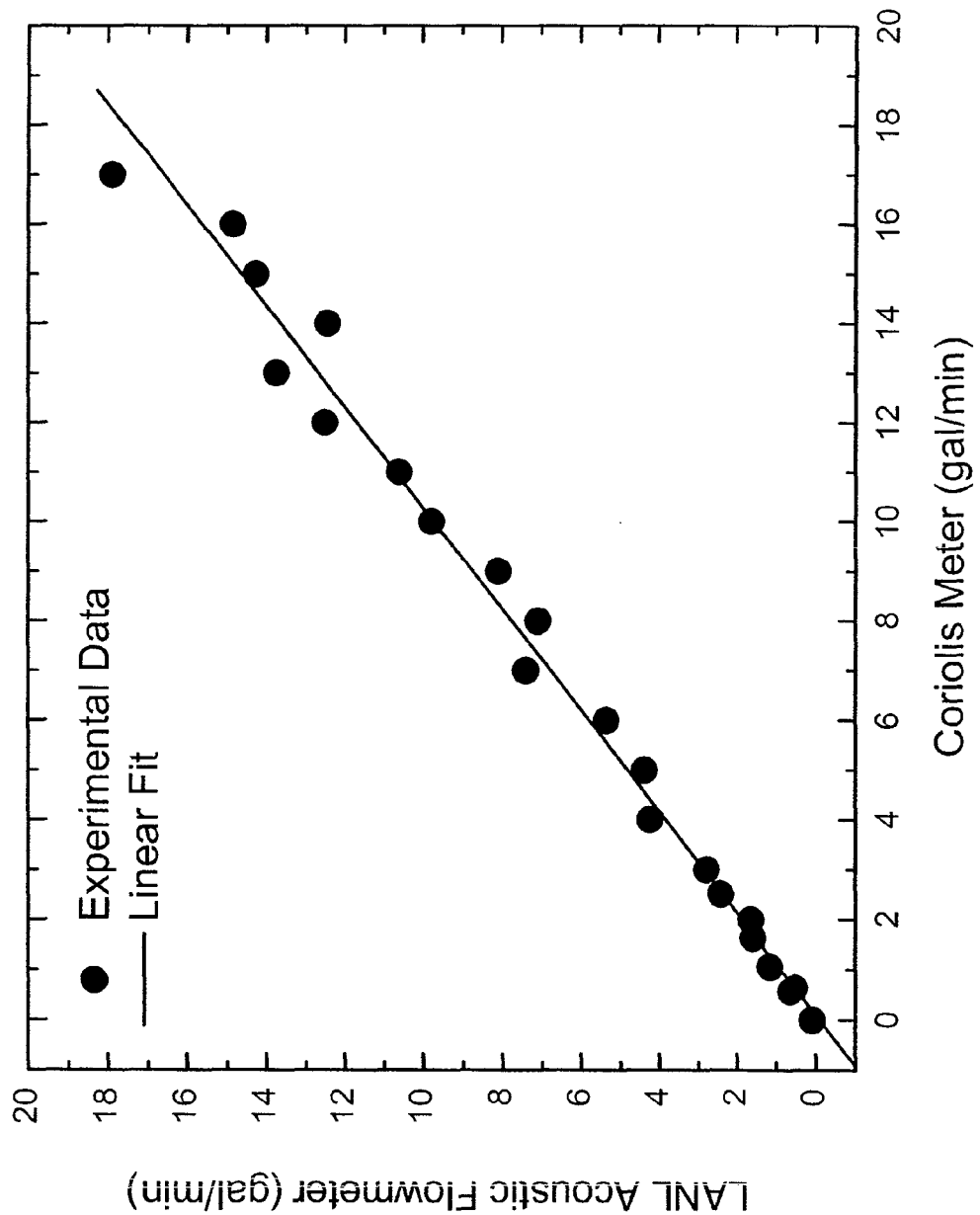
FIG. 12 shows measurements made with an embodiment of the present invention in a crude oil/water mixture compared to measurements made with a commercial Coriolis flowmeter.

FIG. 12 shows measurements in a crude oil-water mixture through a 3-in. diameter pipe which agrees well with the data taken using a commercial Coriolis flow measurement device. The present flow measurement apparatus does not require calibration and measurements do not depend on the type of fluid being measured; water, oil or mixtures thereof, as examples. Additionally, the presence of gas bubbles does not affect the present measurement apparatus as it would Coriolis flowmeter devices, nor must the fluid be diverted as is required for Coriolis metering.

Figure 13C:
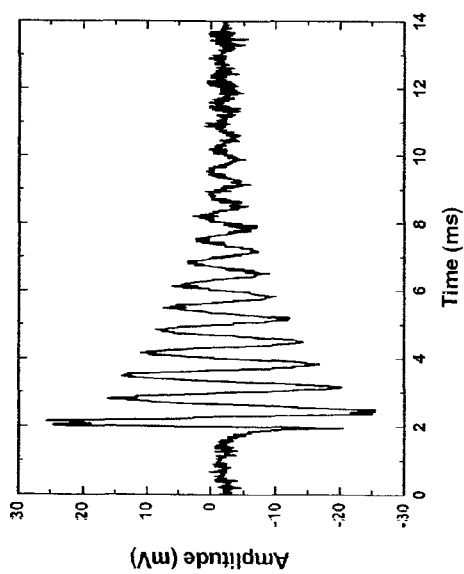
FIG. 13C illustrates the oscillation of multiple bubbles as a function of time.
Figure 13D:
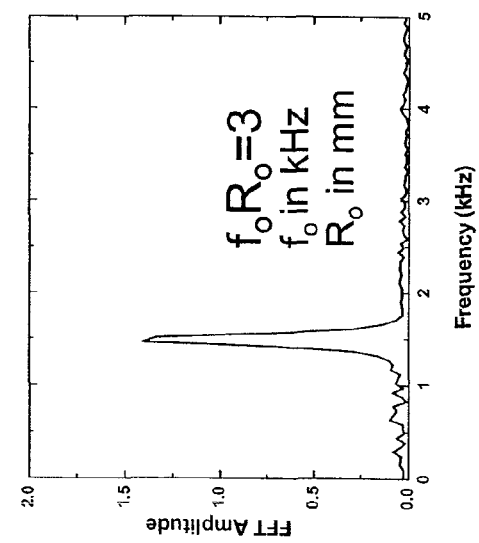
FIG. 13D illustrates the corresponding FFT of the oscillations, the formula for volume (V) as a function of frequency showing that there are two different sizes of bubbles present.
Figure 13A:
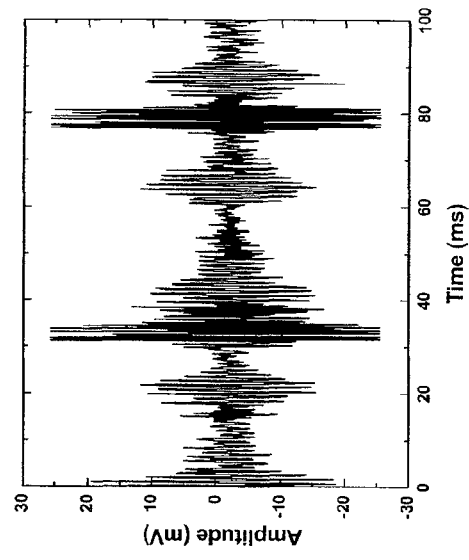
FIG. 13A illustrates the oscillation of a single bubble as a function of time.
Figure 13B:
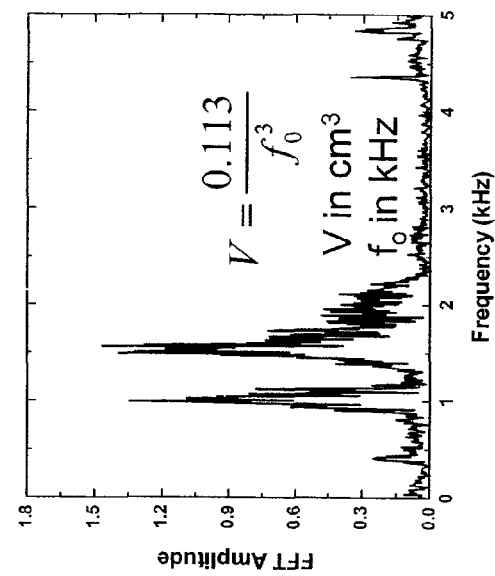

E. Determination of Gas Concentration:

A Doppler measurement permits the determination of the amount of gas flowing through a pipe along with the fluid. The gas may be in the form of bubbles. This is particularly true when the multiphase fluid is driven through a static mixer, which breaks up large volumes of gas and into smaller volumes unless there is a large gas burst. Bubbles moving through a flowing liquid oscillate with a frequency determined by bubble size and the properties of the host fluid. FIG. 13A illustrates the oscillation of a single bubble as a function of time, and FIG. 13B illustrates the corresponding Fast Fourier Transform (FFT) of the oscillation, while FIG. 13C illustrates the oscillation of multiple bubbles as a function of time, and FIG. 13D illustrates the corresponding FFT of the oscillations, the formula for volume (V) as a function of frequency showing that there are two different sizes of bubbles present. In water, the bubble radius R is related to the frequency $f_o$ as $f_o R=3$, where the frequency $f_0$ is in kHz and R is in mm. When there are many bubbles, the area under the curve for the FFT is measured to determine the gas volume.

It is straightforward to obtain this signal through an ultrasonic Doppler measurement using dual-transducer 24 illustrated in FIG. 1A. In this case, a fixed frequency of ultrasound is generated by the transmitter transducer having a certain beam spread and impinges on the gas. The scattered sound beam is Doppler shifted and is detected by the receiver. The electronics module demodulates the signal and extracts the Doppler shifted signal. The strength of the Doppler signal is a measure of the volume of the gas since large volumes scatter more sound, while the frequency shifted signal contains information on the speed of the gas movement and its oscillations. The required information is obtained using joint timefrequency analysis.

Large quantities of gas may block sound transmission through the pipe as is observed for other ultrasonic measurements, such as frequency chirp measurements and flow measurements. By measuring the time period when there is no sound transmission, it is possible to derive information on the quantity of gas that has passed through the pipe. For small quantities of gas, Doppler measurements may be used. Additional information concerning apparatus and methods for such analyses may be found in patent application Ser. No. 13/225,750 for "Apparatus and Method For Noninvasive Particle Detection Using Doppler Spectroscopy", by Dipen N. Sinha filed on 6 Sep. 2011, the entire contents of said patent application being hereby incorporated by reference herein for all that it discloses and teaches.

In an embodiment of the present invention, the transducers used comprise piezoelectric transducers (PZTs) that can withstand continuous temperatures up to 300° F. without degradation. The transducers are rectangular shaped, but curved along their long axis to match the curvature of the pipe, and may comprise bare crystals having wrap-around electrodes whereby electrical connections can be made on the same side of the crystal, leaving unencumbered the surface to be attached to the pipe wall. The center frequency of the transducers is chosen between about 3 and approximately 7 MHz depending on the intended application. For high watercut applications, higher frequencies may be used since sound attenuation is not high, while lower frequency transducers are better suited for high oil-cut applications or in situations where the signal may become attenuated at high frequencies. The transducers may be made broad-band by coating the back side with tungsten loaded epoxy, and the electronics are designed in such a manner that almost any transducer pair can be used for any type of measurement, such as slow sweep, fast chirp, or fixed-frequency operation, with various combinations being possible. Slow sweep measurements taking several seconds to complete are used for high quality measurements and to accurately determine pipe wall thickness mode resonances, which is helpful for flow measurements and also for the Doppler measurements to determine maximum sound transmission. By using resonance transmission, the transmitter signals do not have to be high.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A system for noninvasively measuring multiple independent physical parameters of a multiphase fluid comprising at least one liquid component and gas bubbles flowing in a pipe having a wall, an outside surface and an axis, comprising:
   a first transmitting transducer in ultrasonic communication with the outside surface of said pipe;
   a first waveform generator for generating a frequency chirp signal for driving said first transmitting transducer;
   a first receiving transducer in ultrasonic communication with the outside surface of said pipe diametrically opposed to said first transmitting transducer for receiving the frequency chirp signal from said first transmitting transducer after the chirp signal passes through said multiphase fluid, and for generating a first electrical signal in response thereto;
   means for receiving the first electrical signal from said first receiving transducer and the frequency chirp signal generated by said waveform generator, and for generating speed of sound and sound attenuation information therefrom, from which the composition of the at least one component of said multiphase fluid is determined;
   a second transmitting transducer in ultrasonic communication with the outside surface of said pipe;
   a third transmitting transducer in ultrasonic communication with the outside surface of said pipe disposed a known distance along the axis of said pipe from said second transmitting transducer;
   a second waveform generator for generating a first fixed frequency signal for driving said second transmitting transducer and said third transmitting transducer;
   a second receiving transducer in ultrasonic communication with the outside surface of said pipe diametrically opposed to said second transmitting transducer for receiving the first fixed frequency signal from said second transmitting transducer after the first fixed frequency signal passes through said multiphase fluid, and for generating a second electrical signal in response thereto;
   a third receiving transducer in ultrasonic communication with the outside surface of said pipe diametrically opposed to said third transmitting transducer for receiving the first fixed frequency signal from said third transmitting transducer after the fixed frequency signal passes through said multiphase fluid, and for generating a third electrical signal in response thereto;
   means for receiving the second electrical signal and the third electrical signal, whereby a disturbance in the fluid affecting the second electrical signal will affect the third electrical signal at a later time from which the flow rate of said multiphase fluid is calculated;
   a fourth transmitting transducer in ultrasonic communication with the outside surface of said pipe;
   a third waveform generator for generating a second fixed frequency signal for driving said second transmitting transducer;
   a fourth receiving transducer in ultrasonic communication with the outside surface of said pipe disposed in the vicinity of said fourth transmitting transducer at the same position along the axis of said pipe as said fourth transmitting transducer for receiving a Doppler shifted second fixed frequency signal resulting from reflection from said gas bubbles, and for generating a fourth electrical signal in response thereto; and
   means for receiving the fourth electrical signal and the second fixed frequency signal from said third waveform generator, and for determining the signal strength of the Doppler shifted second fixed frequency signal from which the volume of said gas bubbles is determined.

2. The apparatus of claim 1, further comprising a temperature sensor for determining the temperature of said multiphase fluid for correcting the measured speed of sound.

3. The apparatus of claim 1, wherein said first transmitting transducer, said first receiving transducer, said second transmitting transducer, said second receiving transducer, said third transmitting transducer, said third receiving transducer, said fourth transmitting transducer and said fourth receiving transducer comprise piezoelectric transducers.

4. The apparatus of claim 3, wherein said fourth transmitting transducer and said fourth receiving transducer comprise a dual element transducer.

5. The apparatus of claim 1, further comprising means for determining the affect of said multiphase fluid on thickness mode resonances of the wall of said pipe, whereby the density of said multiphase fluid is determined.

6. The apparatus of claim 1, further comprising means for determining the frequency shift of the received Doppler shifted second fixed frequency signal resulting from reflection from said gas bubbles, whereby the flow rate of said multiphase fluid is determined.

7. The apparatus of claim 1, wherein said means for receiving the first electrical signal from said first receiving transducer and the frequency chirp generated by said waveform generator, performs cross-correlation, and Fast Fourier Transformations thereon.

8. The apparatus of claim 1, wherein the at least one component of said multiphase fluid comprises a liquid hydrocarbon or oil, and water, and said gas bubbles comprise at least one hydrocarbon.

9. The apparatus of claim 1, wherein the frequency chirp signal comprises frequencies between about 100 kHz and approximately 10 MHz.

10. The apparatus of claim 9, wherein the frequency chirp signal has a duration between about 10 μs and 10 ms.

11. The apparatus of claim 1, wherein the disturbance comprises a local inhomogeneity in said multiphase fluid.

12. The apparatus of claim 11, wherein the local inhomogeneity comprises density fluctuations and bubbles in said multiphase fluid.

13. A method for noninvasively measuring multiple independent physical parameters of a multiphase fluid comprising at least one liquid component and gas bubbles flowing in a pipe having a wall, an outside surface and an axis, comprising:
   generating a frequency chirp signal for driving a first transmitting transducer in ultrasonic communication with the outside surface of said pipe;
   receiving the generated frequency chirp signal on a first receiving transducer in ultrasonic communication with the outside surface of said pipe diametrically opposed to the first transmitting transducer after the chirp signal passes through said multiphase fluid, and generating a first electrical signal in response thereto;
   receiving the first electrical signal and the generated frequency chirp signal, and generating speed of sound and sound attenuation information therefrom, from which the composition of the at least one component of said multiphase fluid is determined;

generating a first fixed frequency signal for driving a second transmitting transducer in ultrasonic communication with the outside surface of said pipe, and a third transmitting transducer in ultrasonic communication with the outside surface of said pipe disposed a known distance along the axis of said pipe from the second transmitting transducer;

receiving the first fixed frequency signal on a second receiving transducer in ultrasonic communication with the outside surface of said pipe diametrically opposed to the second transmitting transducer after the first fixed frequency signal passes through said multiphase fluid, and generating a second electrical signal in response thereto;

receiving the first fixed frequency on a third receiving transducer in ultrasonic communication with the outside surface of said pipe diametrically opposed to the third transmitting transducer after the first fixed frequency signal passes through said multiphase fluid, and generating a third electrical signal in response thereto;

receiving the second electrical signal and the third electrical signal and calculating the flow rate of said multiphase fluid from a disturbance in the fluid affecting the second electrical signal and affecting the third electrical signal at a later time;

generating a second fixed frequency signal for driving a fourth transmitting transducer in ultrasonic communication with the outside surface of said pipe;

receiving a Doppler shifted second fixed frequency signal resulting from reflection from said gas bubbles on a fourth receiving transducer in ultrasonic communication with the outside surface of said pipe disposed in the vicinity of the fourth transmitting transducer at the same position along the axis of said pipe as the fourth transmitting transducer and for generating a fourth electrical signal in response thereto; and receiving the fourth electrical signal and the second fixed frequency signal and determining the signal strength of the Doppler shifted second fixed frequency signal from which the volume of said gas bubbles is determined.

14. The method of claim 13, further comprising the step of: determining the temperature of said multiphase fluid; and correcting the measured speed of sound.

15. The method of claim 13, wherein the first transmitting transducer, the first receiving transducer, the second transmitting transducer, the second receiving transducer, the third transmitting transducer, the third receiving transducer, the fourth transmitting transducer and the fourth receiving transducer comprise piezoelectric transducers.

16. The method of claim 15, wherein the fourth transmitting transducer and the fourth receiving transducer comprise a dual element transducer.

17. The method of claim 13, further comprising the steps of: determining the affect of said multiphase fluid on thickness mode resonances of the wall of said pipe, and determining the density of said multiphase fluid therefrom.

18. The method of claim 13, further comprising the steps of: determining the frequency shift of the received Doppler shifted second fixed frequency signal resulting from reflection from said gas bubbles; and determining the flow rate of said multiphase fluid therefrom.

19. The method of claim 13, wherein said step of receiving the first electrical signal from the first receiving transducer and the frequency chirp signal comprises performing cross-correlation, and Fast Fourier Transformations thereon.

20. The method of claim 13, wherein the at least one component of said multiphase fluid comprises a liquid hydrocarbon or oil, and water, and said gas bubbles comprise at least one hydrocarbon.

21. The method of claim 13, wherein the frequency chirp signal comprises frequencies between about 100 kHz and approximately 10 MHz.

22. The method of claim 21, wherein the frequency chirp signal has a duration between about 10 µs and 10 ms.

23. The method of claim 13, wherein the disturbance comprises a local inhomogeneity in said multiphase fluid.

24. The method of claim 23, wherein the local inhomogeneity comprises density fluctuations and bubbles in said multiphase fluid.

25. A method for noninvasively measuring multiple independent physical parameters of a multiphase fluid comprising at least one liquid component and gas bubbles flowing in a pipe having a wall, an outside surface and an axis, comprising:

generating an ultrasonic frequency chirp signal in said multiphase fluid;

receiving the generated frequency chirp signal after the chirp signal passes through said multiphase fluid, and generating a first electrical signal in response thereto;

receiving the first electrical signal and the generated frequency chirp signal, and generating speed of sound and sound attenuation information therefrom, from which the composition of the at least one component of said multiphase fluid is determined;

generating a first fixed ultrasonic frequency signal and a second fixed ultrasonic frequency signal disposed a known distance along the axis of said pipe from the first fixed frequency signal in said multiphase liquid;

receiving the first fixed frequency signal after the first fixed frequency signal passes through said multiphase fluid, and generating a second electrical signal in response thereto;

receiving the second fixed frequency signal after the second fixed frequency signal passes through said multiphase fluid, and generating a third electrical signal in response thereto;

receiving the second electrical signal and the third electrical signal and calculating the flow rate of said multiphase fluid from a disturbance in the fluid affecting the second fixed frequency electrical signal and affecting the third electrical signal at a later time;

generating a third fixed ultrasonic frequency signal in said multiphase liquid;

receiving a Doppler shifted third fixed frequency signal resulting from reflection from said gas bubbles and generating a fourth electrical signal in response thereto; and receiving the fourth electrical signal and the third fixed frequency signal and determining the signal strength of the Doppler shifted second fixed frequency signal from which the volume of said gas bubbles is determined.

26. The method of claim 25, further comprising the step of: determining the temperature of said multiphase fluid; and correcting the measured speed of sound.

27. The method of claim 25, further comprising the steps of: determining the affect of said multiphase fluid on thickness mode resonances of the wall of said pipe, and determining the density of said multiphase fluid therefrom.

28. The method of claim 25, further comprising the steps of: determining the frequency shift of the received Doppler shifted second fixed frequency signal resulting from reflection from said gas bubbles; and determining the flow rate of said multiphase fluid therefrom.

29. The method of claim 25, wherein said step of receiving the first electrical signal from the first receiving transducer and the frequency chirp signal comprises performing cross-correlation, and Fast Fourier Transformations thereon.

30. The method of claim 25, wherein the at least one component of said multiphase fluid comprises a liquid hydrocarbon or oil, and water, and said gas bubbles comprise at least one hydrocarbon.

31. The method of claim 25, wherein the frequency chirp signal comprises frequencies between about 100 kHz and approximately 10 MHz.

32. The method of claim 31, wherein the frequency chirp signal has a duration between about 10 µs and 10 ms.

33. The method of claim 25, wherein the disturbance comprises a local inhomogeneity in said multiphase fluid.

34. The method of claim 33, wherein the local inhomogeneity comprises density fluctuations and bubbles in said multiphase fluid.

* * * * *